(12) United States Patent
Franza, Jr. et al.

(10) Patent No.: US 7,588,887 B2
(45) Date of Patent: Sep. 15, 2009

(54) STABLE ISOTOPE METABOLIC LABELING FOR ANALYSIS OF BIOPOLYMERS

(75) Inventors: B. Robert Franza, Jr., Seattle, WA (US); Yvan P. Rochon, Sedona, AZ (US)

(73) Assignee: The Regents of the University of Washington, Seattle, WA (US)

( * ) Notice: Subject to any disclaimer, the term of this patent is extended or adjusted under 35 U.S.C. 154(b) by 238 days.

(21) Appl. No.: 10/722,161

(22) Filed: Nov. 25, 2003

(65) Prior Publication Data

US 2005/0003375 A1   Jan. 6, 2005

Related U.S. Application Data

(62) Division of application No. 09/786,066, filed as application No. PCT/US99/19434 on Aug. 30, 1999, now Pat. No. 6,653,076.

(60) Provisional application No. 60/098,598, filed on Aug. 31, 1998.

(51) Int. Cl.
*A61K 49/00* (2006.01)
*C12Q 1/00* (2006.01)
*C12Q 1/68* (2006.01)
*C12N 15/63* (2006.01)

(52) U.S. Cl. .................. 435/6; 424/9.1; 435/4
(58) Field of Classification Search ............... None
See application file for complete search history.

(56) References Cited

U.S. PATENT DOCUMENTS

| 5,338,686 | A | 8/1994 | Hellerstein |
| 5,538,897 | A | 7/1996 | Yates, III et al. |
| 5,910,403 | A | 6/1999 | Hellerstein |
| 6,017,693 | A | 1/2000 | Yates, III et al. |

FOREIGN PATENT DOCUMENTS

WO    WO 98/36095    8/1998

OTHER PUBLICATIONS

"Index of the Protein Sequence Database of the International Association of Protein Sequence Databanks (PIR-International)," *Protein Seq. Data Anal.*, 5:65-192 (Mar. 1993).
Bairoch and Boeckmann, "The Swiss Prot Protein Sequence Data Bank, Recent Developments," *Nucl. Acids Res.*, 21:3093-3096 (Jul. 1, 1993).
Barker et al., "Protein Sequence Database," *Meth. Enzymol.*, 183:31-49 (1990).
Beynon, "Qualitative Analysis By Mass Spectrometer," in *Mass Spectrometry and Its Application to Organic Chemistry*, Elsevier Publishing Co., New York, 294-301 (1960).
Bier, "Stable Isotopes in Biosciences, Their Measurement and Models for Amino Acid Metabolism," *Eur. J. Pediatr.*, 156(Suppl. 1):S2-S8 (Aug. 1997).
Bleasby et al., "OWL-a Non-redundant Composite Protein Sequence Database," *Nucl. Acids Res.*, 22:3574-3577 (Sep. 1994).

Burks et al., "GenBank: Current Status and Future Directions," *Meth. Enzymol.*, 183:3-22 (1990).
Cobelli et al., "Validation of Simple and Complex Models in Physiology and Medicine," *Am. J. Physiol.*, 246:R259-R266 (Feb. 1984).
Eng et al., "An Approach to Correlate Tandem Mass Spectral Data of Peptides with Amino Acid Sequences in a Protein Database," *J. Am. Soc. Mass. Spectrom.*, 5:976-989 (Nov. 1994).
Goshe and Anderson, "Determination of Amino Acid Isotope Ratios by Electrospray Ionization-Mass Spectrometry," *Anal. Biochem.*, 231:387-392 (Nov. 1, 1995).
Halliday and Read, "Mass Spectrometric Assay of Stable Isotopic Enrichment for the Estimation of Protein Turnover in Man," *Proc. Nutr. Soc.*, 40:321-334 (Sep. 3, 1981).
Kahn et al., "EMBL Data Library," *Meth. Enzymol.*, 183:23-31 (1990).
Lee et al., "Mass Isotopomer Analysis: Theoretical and Practical Considerations," *Biol. Mass. Spectrom.*, 20:451-458 (Aug. 1991).
Matthews et al., "Regulation of Leucine Metabolism in Man: A Stable Isotope Study," *Science*, 214:1129-1131 (Dec. 4, 1981).
McCloskey, "Appendix f. Calculation of Isotopic Abundance Distributions," *Meth. Enzymol.*, 193:882-886 (1990).
Patterson et al., "Incorporation of a Stable Isotopically Labeled Amino Acid into Multiple Human Apolipoproteins," *J. Lipid Res.*, 32:1063-1072 (Jul. 1991).
Patterson et al., "Measurement of very low stable isotope enrichments by gas chromatography/mass spectrometry: application to measurement of muscle protein synthesis," *Metabolism*, 46: 943-948 (Aug. 1997).
Patterson, S. "Matrix-assisted laser-desorption/ionization mass spectrometric approaches for the identification of gel-separated proteins in the 5-50 pmol range," *Electrophoresis*, 16(7): 1104-1114 (Jul. 1995).
Sadano et al., "cDNA Cloning and Sequence of a New Type of Actin in Mouse B16 Melanoma," *J. Biol. Chem.*, 263: 15868-15871 (Nov. 5, 1988).
Smith and Rennie, "The Measurement of Tissue Protein Turnover," *Bailliere's Clin. Endocrin. Metab.*, 10:469-495 (Oct. 1996).
Tarver and Schmidt, "The Urinary Sulfur Partition in Normal and Cystinuric Dogs Fed Labeled Methionine," *J. Biol. Chem.*, 167:387-394 (1947).
Yarasheski et al., "Measurement of muscle protein fractional synthetic rate by capillary gas chromatography/combustion isotope ratio mass spectrometry," *Biol. Mass. Spectrom.*, 21:486-490 (Oct. 1992).
Yates, "Database Searching Using Mass Spectrometry Data," *Electrophoresis*, 19:893-900 (Jun. 1998).

*Primary Examiner*—Christopher S. F. Low
*Assistant Examiner*—Michele K. Joike
(74) *Attorney, Agent, or Firm*—Townsend and Townsend and Crew LLP

(57) ABSTRACT

Methods for the determination of the rate of synthesis of biopolymer synthesis and degradation in cells, tissues, or cell-free systems using monomer which has been labeled with a stable isotope are provided. Further, the present invention provides methods for the determination or identification of an unknown biopolymer and for the identification of an unknown cell type, a physiological state of a cell or tissue. Also, the present invention provides a database of descriptors which can be used to define an organism, tissue type, cell type, and the like, and which database can be used in conjunction with other public and private databases to identify or characterize an organism, tissue type, cell type, state of differentiation, or physiologic state of an organism, or tissue or cell sample.

10 Claims, 3 Drawing Sheets

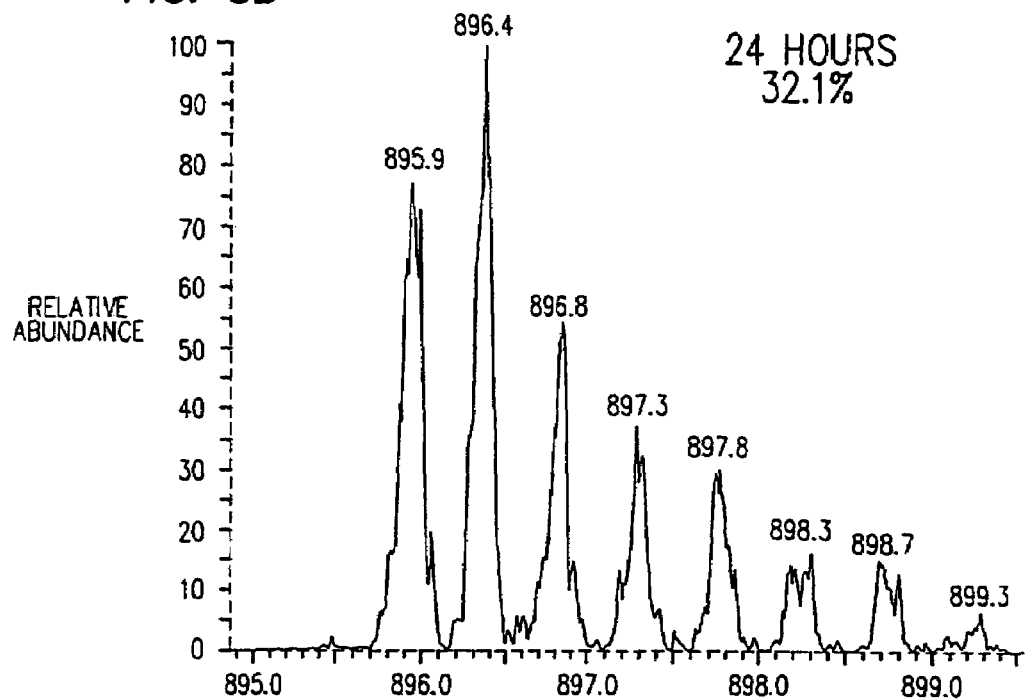
FIG. 3B — 24 HOURS 32.1%
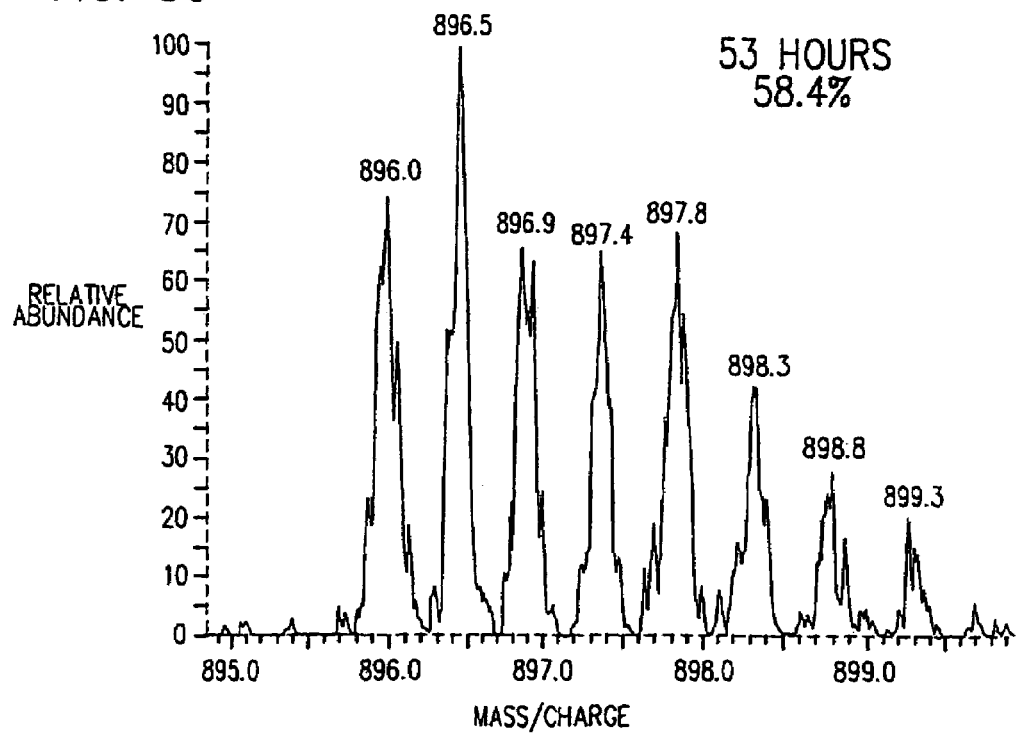
FIG. 3C — 53 HOURS 58.4%

SEQUENCE LISTING

<160> NUMBER OF SEQ ID NOS: 16

<210> SEQ ID NO 1
<211> LENGTH: 16
<212> TYPE: PRT
<213> ORGANISM: Mouse beta actin

<400> SEQUENCE: 1

Ser Tyr Glu Leu Pro Asp Gly Gln Val Ile Thr Ile Gly Asn Glu Arg
 1               5                  10                  15

<210> SEQ ID NO 2
<211> LENGTH: 21
<212> TYPE: PRT
<213> ORGANISM: Mouse beta actin

<400> SEQUENCE: 2

Asp Leu Tyr Gly Asn Val Val Leu Ser Gly Gly Phe Thr Met Phe Pro
 1               5                  10                  15

Gly Ile Ala Asp Arg
            20

<210> SEQ ID NO 3
<211> LENGTH: 9
<212> TYPE: PRT
<213> ORGANISM: Mouse beta actin

<400> SEQUENCE: 3

Ala Val Phe Pro Ser Ile Val Gly Arg
 1               5

<210> SEQ ID NO 4
<211> LENGTH: 8
<212> TYPE: PRT
<213> ORGANISM: Mouse beta actin

<400> SEQUENCE: 4

Asp Leu Thr Asp Tyr Leu Met Lys
 1               5

<210> SEQ ID NO 5
<211> LENGTH: 11
<212> TYPE: PRT
<213> ORGANISM: Mouse beta actin

<400> SEQUENCE: 5

Ala Val Phe Pro Ser Ile Val Gly Arg Pro Arg
 1               5                  10

<210> SEQ ID NO 6
<211> LENGTH: 16
<212> TYPE: PRT
<213> ORGANISM: Mouse beta actin

<400> SEQUENCE: 6

Ser Tyr Glu Leu Pro Asp Gly Gln Val Ile Thr Ile Gly Asn Glu Arg
 1               5                  10                  15

<210> SEQ ID NO 7
<211> LENGTH: 17
<212> TYPE: PRT
<213> ORGANISM: Mouse beta actin

```
<400> SEQUENCE: 7

Asp Asp Asp Ile Ala Ala Leu Val Val Asp Asn Gly Ser Gly Met Cys
 1               5                  10                  15
Lys

<210> SEQ ID NO 8
<211> LENGTH: 18
<212> TYPE: PRT
<213> ORGANISM: Mouse beta actin

<400> SEQUENCE: 8

Val Ala Pro Glu Glu His Pro Val Leu Leu Thr Glu Ala Pro Leu Asn
 1               5                  10                  15
Pro Lys

<210> SEQ ID NO 9
<211> LENGTH: 21
<212> TYPE: PRT
<213> ORGANISM: Mouse beta actin

<400> SEQUENCE: 9

Asp Leu Tyr Gly Asn Val Val Leu Ser Gly Gly Phe Thr Met Phe Pro
 1               5                  10                  15
Gly Ile Ala Asp Arg
            20

<210> SEQ ID NO 10
<211> LENGTH: 10
<212> TYPE: PRT
<213> ORGANISM: Mouse beta actin

<400> SEQUENCE: 10

Ala Gly Phe Ala Gly Asp Asp Ala Pro Arg
 1               5                  10

<210> SEQ ID NO 11
<211> LENGTH: 10
<212> TYPE: PRT
<213> ORGANISM: Mouse beta actin

<400> SEQUENCE: 11

Gly Tyr Ser Phe Thr Thr Thr Ala Glu Arg
 1               5                  10

<210> SEQ ID NO 12
<211> LENGTH: 8
<212> TYPE: PRT
<213> ORGANISM: Mouse beta actin

<400> SEQUENCE: 12

Val Ala Thr Val Ser Leu Pro Arg
 1               5

<210> SEQ ID NO 13
<211> LENGTH: 6
<212> TYPE: PRT
<213> ORGANISM: Mouse beta actin

<400> SEQUENCE: 13

Leu Asp Leu Ala Gly Arg
 1               5
```

```
<210> SEQ ID NO 14
<211> LENGTH: 7
<212> TYPE: PRT
<213> ORGANISM: Mouse beta actin

<400> SEQUENCE: 14

Ile Ile Ala Pro Pro Glu Arg
 1               5

<210> SEQ ID NO 15
<211> LENGTH: 13
<212> TYPE: PRT
<213> ORGANISM: Mouse beta actin

<400> SEQUENCE: 15

Gln Glu Tyr Asp Glu Ser Gly Pro Ser Ile Val His Arg
 1               5                  10

<210> SEQ ID NO 16
<211> LENGTH: 21
<212> TYPE: PRT
<213> ORGANISM: Mouse beta actin

<400> SEQUENCE: 16

Asp Leu Tyr Ala Asn Thr Val Leu Ser Gly Gly Thr Thr Met Tyr Pro
 1               5                  10                  15

Gly Ile Ala Asp Arg
                20
```

STABLE ISOTOPE METABOLIC LABELING FOR ANALYSIS OF BIOPOLYMERS

CROSS REFERENCE TO RELATED APPLICATIONS

This application is a divisional of U.S. application Ser. No. 09/786,066, filed Feb. 28, 2001 now U.S. Pat. No. 6,653,076, which is the U.S. National Stage of International Application No. PCT/US99/19434, filed on Aug. 30, 1999, which claims the benefit of U.S. Provisional Application Ser. No. 60/098,598, filed on Aug. 31, 1998, the complete disclosures of each are expressly incorporated herein by reference in their entirety.

GOVERNMENT SUPPORT

The U.S. government may have certain rights in the invention pursuant to a grant received from the U.S. National Institutes of Health.

FIELD OF THE INVENTION

The present invention relates to methods for measuring and analyzing the synthesis and turnover of polymers within cells or tissues, or during chemical reactions outside of the cell, using components of the polymer containing stable isotopes as probes.

BACKGROUND OF THE INVENTION

Living systems comprise large polymeric structures made up of building blocks or components (monomers) which are themselves made up of elements. Examples of large polymeric structures found in living systems include proteins made up of amino acids, DNA and RNA made up of nucleic acids, complex carbohydrates made up of sugars, and lipids which can include fatty acids. The ability to measure the formation and degradation of polymers within cells or in cell-free systems is integral to understanding regulatory processes controlling cell proliferation and death, and the nature of chemical reactions. The biosynthesis and degradation of a polymer is particularly important to an understanding of various disease processes, development of an organism, cellular differentiation, tissue remodeling, and the like.

Existing methods used for determining polymer formation and degradation within cells or organisms are often referred to as "metabolic labeing" techniques. By far the most common current technique for the in vitro metabolic labeling of cells or tissues in culture uses $^{35}$S-methionine as a probe to measure the formation or degradation of cellular proteins. The technique of using radioactively-labeled amino acids as metabolic probes dates back to the late 1940's (Tarver, et al., *J. Biol. Chem.* 167:387-394 (1947)).

Although the technique is widely used for in vitro determinations of protein synthesis, there are major disadvantages to using radioactive amino acids or other exogenous (where the probe is not a usual constituent of the polymer being studied) radioactive probes in metabolic studies. These disadvantages include: 1) the danger to personnel using ionizing radiation, as well as the necessity to acquire permits for the purchase, storage, and disposal of radioactive materials; 2) the need to collect all of the protein synthesized to permit quantitative determinations since the method measures absolute levels of radioactive signal; 3) exogenous probe often alters the physical properties of the polymer being studied; 4) many elements exist for which there are no known radioactive species; and 5) use of radioactive probes is generally limited to in vitro systems or animal models since the concentration of probe needed for human studies usually exceeds legislated "safe-dose" standards.

These difficulties in the use of radioactive probes can be largely overcome as provided by the present invention by the use of a probe containing a stable isotope.

That most elements are mixtures of a number of stable isotopes has been known for over 60 years, and stable isotopes have been used as probes for metabolic studies within humans. The use of these probes was initially limited by their high cost and limited availability. Over the last few decades, many techniques for the production of stable isotope probes have been developed, and highly purified probes containing stable isotopes are commercially available. Further, instruments for the analysis of isotopic peaks (mass spectrometers) are now readily available to most workers in the field.

Use of a stable isotope for analyzing incorporation of a probe into biopolymers during in vivo metabolic studies has several problems. These problems include but are not limited to: 1) the need to breakdown the biopolymer of interest into smaller components (often amino acids); 2) the need to chemically derivatize the components followed by separating the components within their classes (often by gas chromatography); and 3) analyzing the mass of each component using a mass spectrometer (Halliday and Read, *Proc. Nutr. Soc.* 40:321-334 (1981)).

For each polymer of interest, the steps of separating the components within their classes and analyzing the mass of the components takes between 30 minutes to 1 hour. This greatly restricts the number of different polymers that can be analyzed on any one day. In addition, during the derivatization step, chemicals are added to the components, changing both the mass of the components and the isotope peak ratios in non-trivial ways (Lee et al., *Biol. Mass Spectr.* 20:451-458 (1991); Smith and Rennie, *Biol. Clin. Endocrin. Metab.* 10:469-495 (1996)). As stated by leaders in the field, "The technique is not without its disadvantages: the amino acid derivatization and quality control procedures are laborious and time-consuming; special instrumentation is required for precise GC-MS measurements; and a large number of time points are needed to accurately define the protein kinetics following a single-dose tracer administration." Patterson. B. W., et al., *J. Lipid Res.* 32:1063-1072 (1991); see also, Goshe and Anderson, *Anal. Biochem.* 231:382-392 (1995)).

Despite the limitations inherent in the use and analysis of stable isotopes, widespread acceptance of gas chromatography and mass spectrometry have hindered the development of faster and simpler forms of analysis. As recently stated in a review of the field (Bier, *Eur. J. Pediatr.* 156(1):S2-S8 (1997)), "The worldwide acceptance and primacy of gas-chromatography-mass spectrometry (GCMS) as the preferred analytical tool for identification of abnormal metabolites . . . confirms the general nature of this method, supports the position that its limitations are relatively small in number, and attests to the nearly absolute specificity of metabolite identification using this method".

The scientific and medical community's understanding of physiological processes is currently limited by the speed with which quantitative data can be collected, and the method by which the data is stored and processed in an easily retrievable fashion. Cobelli aptly summarizes this dilemma: "The principal difficulty attached to the mathematical analysis of physilogical and medical systems stems from the mismatch between the complexity of the processes in question and the limited data available from such systems." Cobelli, et al., *Am. J. Physiol.* 246:R259-R266, 1984. Thus, there remains a need in the art to develop high-throughput techniques for measuring polymer synthesis in these complex systems. Quite surprisingly, the present invention fulfills this and other related needs.

SUMMARY OF THE INVENTION

The present invention provides a non-radioactive technique for determining polymer formation or degradation, rapid processing and measurement of a large number of different polymers. In one aspect, the method includes adding a mass isotopically labeled component of a polymer (probe) to a system in which the unlabeled component of the same type as the probe has been depleted. Depleting the cellular pool of unlabeled component prior to adding the labeled probe increases the likelihood that during polymer formation, the labeled probe is incorporated into the new polymer. Over a period of time, the mass isotopically labeled probe will be incorporated into the new polymer formed, and the total pool of that polymer is the sum of the polymer present prior to adding the probe and newly formed polymer which has incorporated the probe.

The polymer of interest is isolated after a desired period of time in the presence of the probe. The isolated polymer can be cleaved into smaller fragments and the mass of the fragment and all isotopic peaks measured using an analytical instrument such as a mass spectrometer. For each fragment, the relative abundance of the different mass peaks from samples containing probe is compared to the mass peaks from samples where probe is absent. The ratios of fragment polymer mass peaks from samples treated with or without the probe are compared mathematically, and the relative proportion of polymer synthesized is determined. In one embodiment, the rate at which the polymer is synthesized is determined by measuring the relative amount of polymer formed at two or more time points, and dividing the difference in polymer synthesized at the different time points by the time interval.

The present invention also provides a method for storing experimental data within a searchable database to determine the identity of an individual polymer within a complex of several different polymers. Initially, an individual polymer can be separated from the complex of polymer, if desired, cleaved into smaller fragments, and the mass of the polymer or resultant fragments determined by an analytical instrument such as a mass spectrometer. For each parent polymer, a specific set of fragments having different masses is generated during the fragmentation procedure, but only a subset of these fragments is found within the mass spectra from the analytical instrument. The set of fragments of specific sizes that is measured by the analytical instrument can be used as a "fingerprint" to identify the parent polymer from which the fragments are derived. The database contains "fingerprints" for a large number of different polymers, and is used to decipher the individual components of a complex comprising a number of polymers.

The process of measuring the relative amount and rate of polymer formation within cells or during a chemical reaction includes adding a labeled monomer probe containing one or more molecules of a stable isotope of an element within the structure of the monomer to cells growing in tissue culture or to a chemical reaction outside of a cell. After the desired incubation time in the presence of the monomer probe, a sample is taken and the chemical reaction is stopped. Products of the reaction are isolated and the relative abundance of the monoisotopic and isotopomeric peaks of the polymer produced are measured and compared to the relative abundance of the monoisotopic and all isotopomeric peaks of the polymer produced from a similar chemical reaction where no labeled monomer probe has been added. In the case of living cells, the cells are washed free of unincorporated monomer probe and solubilized to free the individual biopolymer, i.e., proteins, lipids, nucleic acids, complex carbohydrates, and the like. The resultant cellular polymers can then be separated and isolated by common techniques, and if desired, further fragmented enzymatically and the relative abundance of the monoisotopic and all isotopomeric peaks of the polymer or fragments thereof measured. The measured abundance for a test sample is then compared to the relative abundance of the monoisotopic and isotopomeric peaks of polymer isolated from solubilized cells treated in the same way except for the addition of monomer probe.

To determine the relative amount of polymer formed during a desired incubation time, a mathematical algorithm (Equation (1)) is applied to the comparison of the relative abundance of the monoisotopic and isotopomeric peaks from whole or fragmented polymers in the presence and absence of the probe.

$$\left(1 - \frac{\sum_C}{\sum_S}\right) \times 100 \qquad (1)$$

To determine the rate of polymer synthesized or degraded, the relative amount of polymer is measured over two or more time-points and is equal to the slope of the line represented by the percent abundance of labeled polymer per unit time. When samples are taken at two time points the rate of synthesis or degradation is equal to the percent of labeled polymer at time 2 divided by the percent of labeled polymer at time 1.

The present invention also provides a database comprising mass spectra obtained for the polymers and polymer fragments in relation to particular descriptors. The mass spectra define a polymer or fragment thereof by the quantity of mass isotopically labeled monomer over a specified time period. A mass spectra for one or more polymers or a fragment of the polymers is used to characterize a particular protein found in a cell or tissue at a particular stage of development, differentiation, or physiological state.

In practicing the methods of the present invention to determine the rate of polymer synthesis or degradation, the data obtained for each polymer and polymer fragment analyzed for a particular population of cells can be entered into a database with associated descriptors. The descriptors include such characteristics as the species of organism, cell type, tissue type, state of differentiation, polymer class, method of separation of polymer class into separate parent polymers, method of fragmentation of parent polymer, and the like. Having established a database, an unknown cell, tissue sample or polymer is labeled with a stable isotopic monomer probe and the abundance of the labeled probe at certain time points determined. The rate of incorporation of the labeled probe and/or the "fingerprint" of fragments obtained for the parent polymer by a particular method is compared to the database, and one or more matches within the database can then be determined to identify the organism, cell, tissue type, polymer, etc. The "fingerprint" can also be compared to private or public databases comprising amino acid or nucleic acid sequence information, for example, or a monomer sequence can be determined for the isolated parent polymer or fragment thereof to identify the parent polymer. The data obtained for the unknown sample can be added to the database with all known descriptors to increase the size of the database.

BRIEF DESCRIPTION OF THE DRAWINGS

FIG. 1A depicts the distribution of the peaks for the peptide SYELPDGQVITIGNER (SEQ ID NO. 1), a +2 peptide with a monoisotopic mass of 1790.9, and FIG. 1B depicts the distribution for the peptide DLYGNVVLSG-GFTMFPGIADR (SEQ ID NO. 2), a +2 peptide with a monoisotopic mass of 2230.5. The y-axis represents the relative abundance of each monoisotopic and isotopomeric peak. The x-axis represents the mass per charge on the peptide. Since both peptides have a charge of +2, the monoisotopic map measured by the mass spectrometer is the molecular mass of the peptide divided by 2, plus 1 for an added hydrogen molecule.

FIGS. 3A-3C depict the mass peak distribution for the mouse actin peptide SYELPDGQVITIGNER (SEQ ID NO: 1). FIG. 3A depicts the peak mass distribution for the peptide from a control sample. FIG. 3B depicts the mass peak distribution for the peptide from a sample grown in the presence of $^{15}N$-isoleucine and $^{15}N$-leucine for 24 hours. FIG. 3C depicts the mass peak distribution for the peptide from a sample grown in the presence of $^{15}N$-leucine for 53 hours (the peptide contains 2 isoleucine residues and one leucine). for all three panels, the spectra shown have normalized sums of the ion peaks which were virtually identical to the means of the sums calculated for all of the spectra analyzed for the peptide (control, n=23; 24 hrs., n=17; 53 hrs., n=12).

DESCRIPTION OF THE SPECIFIC EMBODIMENTS

Figure 1A:
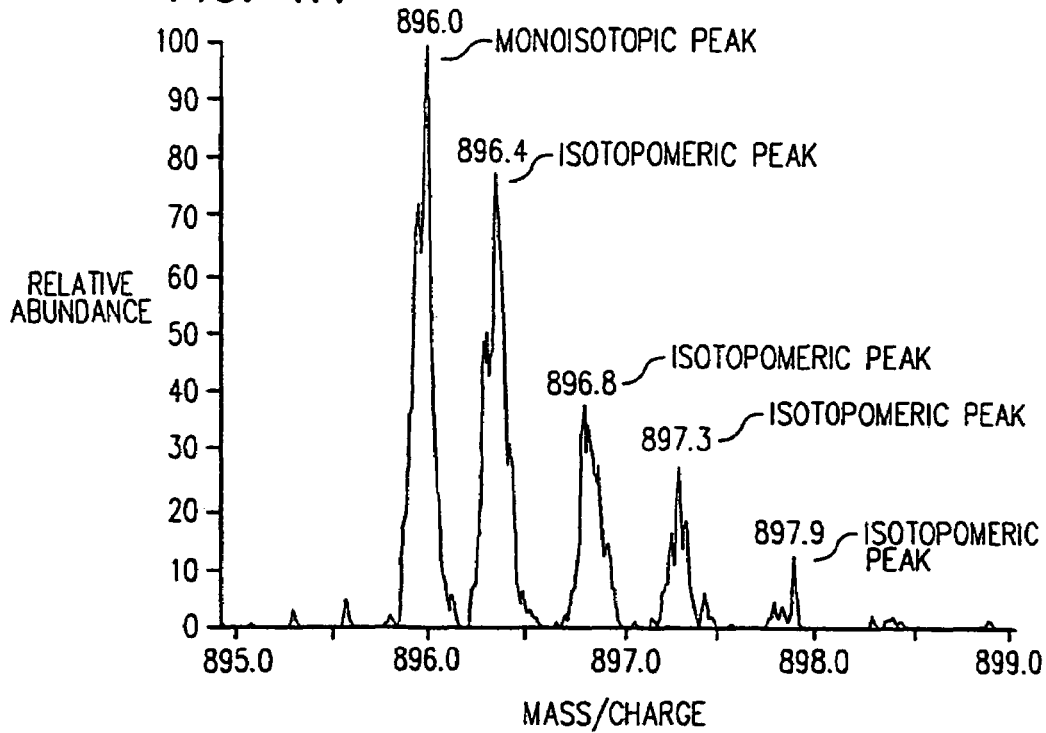
FIGS. 1A and 1B depict examples of the distribution of the monoisotopic and isotopomeric peaks for two peptides from mouse actin, where
Figure 1B:
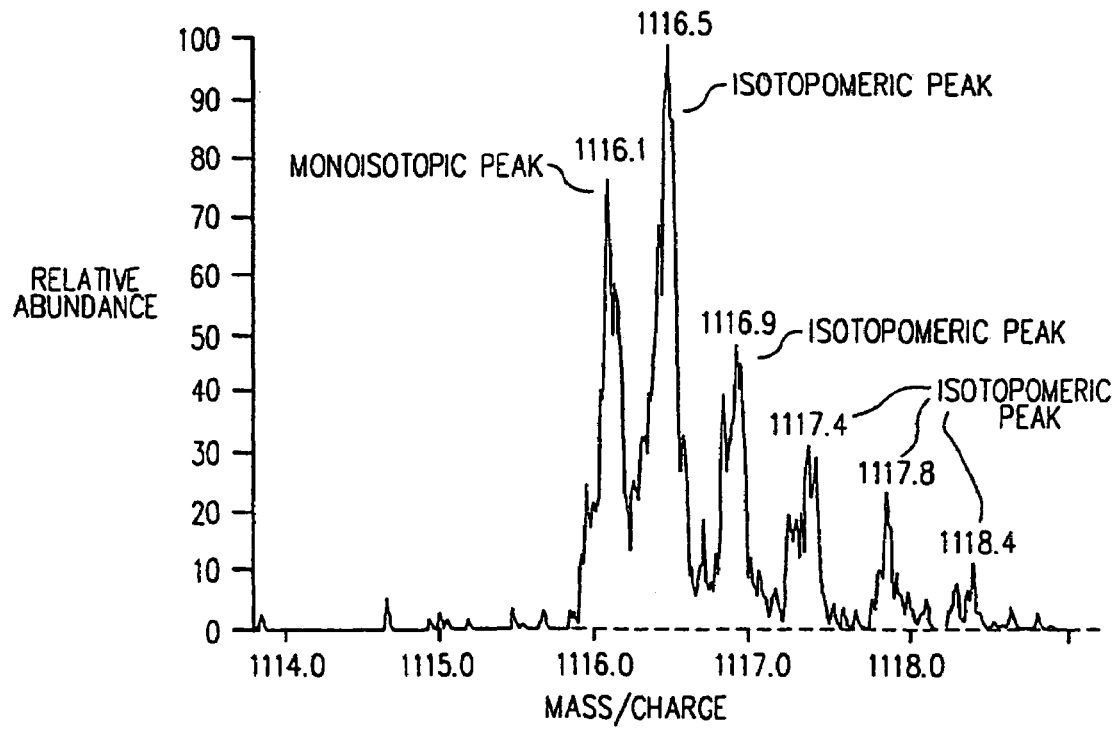
Figure 2:
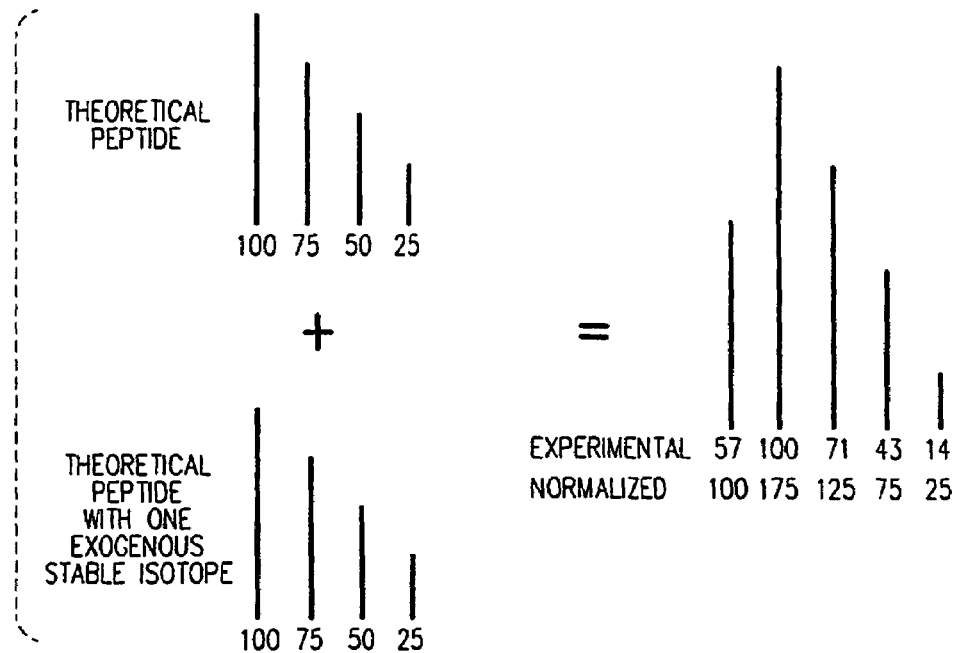
FIG. 2 depicts a diagram demonstrating the theory behind the determination of biopolymer synthesis using stable isotopes. Shown is a theoretical peptide from a protein with the most abundant peak (the monoisotopic peak) set at 100, the first isotopic peak set at 75, the second at 50, and the third at 25. (The sum of the peak heights equals 250). A theoretical peptide containing the identical amino acid sequence but with one of the amino acids fully substituted with a $^{15}N$ will essentially give an identical isotope spectra shifted one mass unit higher. Mixing a 50% solution of the unsubstituted peptide with a 50% solution of the substituted peptide will give an isotope spectra which is a mixture of the two spectra found for the individual peptides. Normalzing the monoisotopic peak to 100, and all other peaks at this spectra based on a monoisotopic peak will give a sum of peak heights equal to 500. The percent of peptide containing probe within the mixture can be determined using equation 1.

Prior to setting forth the invention, it may be helpful to an understanding thereof to set forth definitions of certain terms to be used hereinafter.

As used herein, the term "polymer" or "biopolymer" refers to a molecule, such as a protein or polypeptide, an oligonucleic acid (DNA and RNA), a complex carbohydrate, or a lipid, made up of discrete "components." In the present application "component(s)" refers to a monomer which makes up a biopolymer, i.e., amino acids (for proteins), nucleic acids (for DNA and RNA), sugars (for complex carbohydrates), and fatty acids (for lipids). The "components" are themselves made up of elements such as carbon, oxygen, and nitrogen. These elements have a measurable mass.

"Stable isotopes" of elements as used herein defines an isotope of an element having identical numbers of protons and electrons, but having an additional neutron, which increases the molecular weight of the element by one mass unit.

The "monoisotopic mass" of a polymer or a fragment thereof as used herein defines the molecular weight of the polymer or of a fragment thereof in the absence of any naturally occurring stable isotope of the elements making up the polymer or a fragment thereof.

The "isotopomeric masses" of a polymer or fragments thereof are all of the different combinations of the polymer or fragment in the presence of any naturally occurring stable isotope of the elements making up the polymer or a fragment thereof.

"Mass spectrometry" refers to an analytical tool used to measure the mass or the mass per charge of polymers or their fragments. These methods can include "MALDI-MS" which refers to a type of mass spectrometry using Matrix Assisted Laser Desorption Ionization, where whole or cleaved polymers are mixed with a matrix substrate on a surface, and ionized by a laser direct laser desorption ionization mass spectrometry (with no matrix), electrospray ionization mass spectrometry, secondary neutral mass spectrometry, secondary ion mass spectrometry, and the like.

In one embodiment the invention provides a method for determining the rate of in vitro synthesis of a polymer (biopolymer) during a defined time interval using a stable isotope labeled monomer component as a probe. The method comprises the general steps of:

(a) isolating a population of cells or tissue from an animal;

(b) culturing the isolated population of cells in a culture medium capable of maintaining the viability of the cells, wherein the culture medium comprises at least one component monomer of the biopolymer;

(c) removing from the culture medium one or more component monomers of a polymer class to deplete the component from the intracellular cellular pool of component monomer;

(d) admixing with the isolated cells a culture medium comprising the depleted monomer component with a labeled form of the component as a probe, wherein the label is a stable isotope of an element, for a time period sufficient for incorporation of labeled probe into the polymer class;

(e) isolating from the isolated cell the polymer class at one or more predetermined time points;

(f) determining the relative abundance of monoisotopic and isotopomeric mass peaks for the polymer class at each time point; and (g) comparing the relative abundance of the monoisotopic and isotopomeric for the polymer class at each time point to determine the rate of polymer formation.

In a related aspect the polymer class is further separated by a physical characteristic which can distinguish individual parent polymers within the polymer class. In one embodiment, the separated parent polymer can be fragmented.

These steps are described in greater detail below, and an illustration of the practice of the method is provided in the examples.

The method of the present invention is particularly useful for determining the rate of polymer formation or synthesis in cells maintained in long term culture or cells which have been recently isolated from an animal. Cells recently isolated are usually referred to in the art as a primary culture. Examples include, but are not limited to, tumor cells, blood cells, and cells isolated from a particular tissue. Methods for maintaining long term cell cultures and cells of a primary culture are well known to the skilled artisan. The methods of the present invention are also considered useful for determining the rate of polymer synthesis in cell free systems, such as, e.g., a reticulocyte lysate translation system.

As used in the present invention, mass isotopically labeled components, or monomer subunits, can be distinguished from naturally occurring, non-labeled components, by being one mass unit heavier. The stable isotopes of common elements useful in the methods of the present invention include, but are not limited to, carbon ($^{13}C$), hydrogen ($^{2}H$), oxygen ($^{18}O$), and nitrogen ($^{15}N$). These stable isotopes are available commercially as elements or incorporated into components of a biopolymer. In particular, $^{15}N$-labeled basic sugars (such as, glucose), amino acid residue components of proteins, [basic sugars, such aas glucose], and the like, are available commercially. In the practice of the present invention it is preferred that the labeled element or component be stable, and that any preparation containing the labeled component be at least more than about 85% typically more than 95%, and preferably more than about 98% enriched with the stable isotope or isotopes. A high level of enrichment is preferred to ensure that the majority of the component monomer incorporated into newly synthesized polymer is labeled.

Generally, it is preferred in the practice of the invention that the stable isotope-labeled component, or probe, not be synthesized or formed endogenously by the cells or tissues of interest, or during a cell-free reaction. That is, exogenous addition of the labeled component should be necessary for the polymerization reaction to occur, or for the cell or tissue to remain viable. It is also preferred that the component selected as the probe be capable of being either actively or passively transported across the cellular membrane in both the unlabeled and labeled form. Examples of component monomers suitable for the practice of a method of the present invention and the biopolymers they form are listed in Table 1.

TABLE 1

Representative Biopolymer Components

| Component | Biopolymer |
| --- | --- |
| acetyl coA | fatty acid/lipids |
| ribonucleic acids | RNAs |
| deoxyribonucleic acids | DNAs |
| amino acids (i.e. Leu, Ile, Arg) | peptides/proteins |

It is also preferred that a stable isotope-labeled component is selected so that during a desired time for incorporation one or more molecules of the labeled monomer will be incorporated into a newly synthesized polymer. In addition, a more accurate measurement of the rate of synthesis of a polymer species produced in large quantities over a short period of time can be obtained if essentially all of the unlabeled cellular pool of the monomer used for the probe is depleted from the cell or reaction mixture prior to admixing the component with the isolated cells, tissues or reaction mixture. By depleting essentially all of the unlabeled monomer from the cell or reaction prior to adding the labeled probe essentially only labeled monomer will be incorporated into newly synthesized polymer. Therefore, the time of addition of the labeled probe can be more accurately defined as the zero time point.

One advantage of labeling biopolymers with stable isotopes for the analysis of biopolymer synthesis over the use of radioactive isotopes is eliminating the need to collect all of the protein for accurate measurements of biopolymer synthesis. The determination of the extent of new biopolymer synthesized is calculated from a ratio of the relative abundance of protein present before and after the addition of the labeled probe. Therefore, the determination of synthesis rates is unaffected by the fraction of the total pool of biopolymer collected upon isolation of the parent polymer. With radioactive labeling, loss of biopolymer during the preparatory steps (which varies depending on the biopolymer) can lead to under-representation of the actual amount of protein synthesized. In addition, the absolute value of radioactivity measured for biopolymer on electrophoretic gels can depend on the number of labeled monomers within the biopolymer. For example, a protein labeled with $^{35}S$-methionine containing 10 methionine residues will have the same absolute value of radioactivity as 5 times more of a protein containing only two methionine residues.

Rather than labeling newly translated biopolymer-with enough stable isotope so the mass of the labeled biopolymer is not subject to interference from the isotope cluster of the endogenous unlabeled biopolymer, or filly substituting them with a large number of altered monomer molecules, it is preferred to substitute one or two stably labeled essential amino acids. This enables more accurate measurement of identical peptides when comparing control samples to samples where the labeled monomer had been incorporated.

In the case of proteins, a further advantage of limiting the number of labeled amino acids within each peptide is that it keeps the mass of the labeled peptide within the range of the isotopomeric peaks of the parent or unlabeled peptide. By having the mass spectra of the labeled peptide overlap the mass spectra of the parent peptide, calculations of the extent of label incorporation can be easily accomplished using the ratio of the mass peaks to one another. Such overlap is important when only small amounts of protein are synthesized because it ensures that the mass spectra of the peptide incorporating the probe is not diluted by background noise. By limiting the number of probes incorporated into each peptide, small shifts in mass peaks due to incorporation of probe are added to naturally occurring isotope peaks that are already significantly above background. In determining a rate of polymer synthesis using the method of the present invention, cells or tissues are incubated with the labeled monomer probe for a period of time sufficient for at least one, and preferably more molecules of the probe to be incorporated into a polymer. It is preferred that the period of incubation be at least 30 minutes, and can be up to 24 to 72 hours, or more.

In a particular embodiment of the present invention $^{15}N$-leucine and $^{15}N$-isoleucine were used as the stable isotope-labeled components to measure the rate of synthesis of β-actin in a murine T cell line stimulated to proliferate in culture.

The labeled amino acids were added to the culture medium surrounding the cells and a mitogen was added to stimulate proliferation of the cells initiating the incorporation of the labeled amino acid monomer into newly synthesized polymer protein. Samples of the proliferating cells were taken at predetermined time points for the determination of the rate of protein synthesis. The addition of stable isotopically labeled amino acid(s) into the culture medium surrounding the cells resulted in the uptake of the labeled amino acid residues into the cell, and the isotopically labeled amino acid probe into newly synthesized proteins, including β-actin.

In practicing the methods of the present invention it is typically preferred that the biopolymers are isolated by class. As used in the present invention a polymer class is defined as biopolymer comprising primarily one type of component monomer. For example, the major polymers of a biological system include DNA, RNA, protein or polypeptides, complex carbohydrates and lipids, as set forth above. Methods for isolating a particular polymer class are well known to the skilled artisan and the methods of the present invention are not intended to be limited by a method used in the isolation of a particular polymer class or polymer.

Representative isolation methods include lysing a cell by chemical or mechanical means, or a combination thereof, followed by, in any combination or order, gel filtration, affinity chromatograph, chemical extraction, precipitation, differential solubilization, and the like. For example, to isolate proteins or polypeptides from cellular material, it is typical for a cell sample to be collected and washed prior to lysing the cells with a lysis buffer. Generally, a lysis buffer comprises a membrane solubilizing agent (i.e., a detergent), reducing agent, agents to break down oligonucleotides (i.e., enzymes) and various buffers. After cell lysis and the removal of large cellular material and other insoluble material, the proteins and polypeptides can be separated by any of a number of physical characteristics, including but not limited to, size, charge, ligand affinity, and the like.

Oligonucleotides can be separated from other cellular biopolymers and cellular material by, for example, lysing the cells in the presence of nuclease inhibitors, various proteases to break down proteins, and buffering and solubilizing agents.

Oligonucleotides can then be separated from the remaining cellular material by, for example, phenol/chloroform extraction and precipitation. Well known methods are available for the isolation of RNA or DNA if desired. The isolated nucleic acids can then be fragmented by chemical or enzymatic digestion, or by a mechanical means and the resultant fragments separated by, for example, size.

Lipids, which primarily make up the various membranes of a cell, can be extracted using various organic extraction methods. Certain fatty acids and the like can be isolated by, for example, saponification. Various other methods are well known to the skilled artisan.

Complex carbohydrates can be associated with or comprise a portion of another biopolymer, such as, e.g., glycoprotein or glycolipid. To quantitate the rate of synthesis of a particular complex carbohydrate associated with a biopolymer, the biopolymer is isolated prior to removing the carbohydrate. The complex carbohydrate can than be cleaved from the biopolymer by any number of means known to the skilled artisan, including, but not limited to, sodium borohydride, or enzymatic digestion.

Once the desired class of biopolymer has been isolated the biopolymer class can be separated into parent polymer molecules having a range of physical characteristics. In a preferred embodiment of the present invention, the isolated parent polymer can be further fragmented. For example, an isolated protein or a polypeptide from an activated T-cell can be isolated and separated by molecular weight and/or isoelectric point using two dimensional electrophoresis. This separation results in a number of spots on the second dimension gel comprising proteins and polypeptides which have approximately the same molecular weight and have approximately the same isoelectric point. The parent proteins and polypeptides present in a spot can be further fragmented by admixing a chemical, such as, for example, cyanogen bromide, or a protease, including, for example, trypsin, chymotrypsin, or papain, with an excised gel spot. Enzyme digestion results in a number of peptides for each parent polymer. Each particular protein or polypeptide within a spot will have a specific particular enzyme fragment pool or "fingerprint" produced within the desired time period the rate of synthesis is determined.

Fragmentation of other biopolymers, for example DNA or RNA, can be accomplished by cleavage using a restriction enzyme or mechanical means. Complex carbohydrates can be fragmented by chemical means or by means of an enzyme. Lipids can be fragmented by chemical means or by means of an enzyme, including for example, a lipase. Once the biopolymer has been fragmented, the various fragments can be separated by means well known in the art. These methods include, but are not limited to, gel filtration, electrophoresis, affinity chromatography, and the like. The abundance of monoisotopic and isotopomeric peaks can then be determined for each fragment of biopolymer label and associated with the particular cell or tissue from which it was isolated.

For the purposes of the present invention, monoisotopic and isotopomeric abundance can be determined by an analytical instrument capable of accurately measuring the mass of a polymer or fragment thereof. For example, mass spectrometry can be used. Mass spectrographic methods can include, but are not limited to, matrix assisted laser desorption ionization-mass spectrometry (MALDI-MS), direct laser desorption ionization mass spectrometry, electrospray ionization mass spectrometry, secondary neutral mass spectrometry, secondary ion mass spectrometry, and the like.

The abundance of the monoisotopic and isotopomeric peaks can be expressed in a number of ways, but is typically expressed by scoring the highest or most abundant peak as 100%. All other peaks within the mass spectra for the polymer or fragment thereof are compared to the most abundant peak. To determine the relative abundance of each mass peak, peak heights or the area under the curve can be used. In unlabeled samples, and for large polymers or polymer fragments, the most abundant peak measured is usually found to be the first or second isotopomeric peak rather than the monoisotopic peak because of the incorporation of more than one labeled component monomer. For the purposes of the present invention, typically the whole spectra of monoisotopic and isotopomeric peaks determined from a labeled sample are compared to the whole spectra from an unlabeled sample.

In one embodiment of the method a control sample is collected and the abundance of the monoisotopic and isotopomeric peaks is measured to determine the proportion of monoisotopic and naturally isotopomeric peaks found in the sample prior to labeling. Samples are also collected at various predetermined time points following the addition of the mass isotopically labeled monomer probe. To be of general use the time interval between the addition of the labeled probe and the time of sampling should be large enough to allow substantial incorporation of the labeled probe into newly synthesized polymer. In some embodiments, test sampling can be carried out at about 12 to 24 hours, and up to 72 hours, or more. The abundance of monoisotopic and isotopomeric peaks measured from the spectra obtained for a biopolymer isolated from the test sample is compared to the abundance of monoisotopic and isotopomeric peaks obtained for the same biopolymer isolated from a control sample. This comparison provides a characteristic analysis for the cell or tissue being examined based on any observed change in the monoisotopic and isotopomeric peaks for the polymer in question.

According to another aspect of the present invention, the rate of synthesis of one or more particular polymers present in a cell or tissue can also be determined by measuring the level of newly synthesized polymer at two or more different time points. The method comprises:

(a) calculating the sum of the normalized peak heights for the control polymer ($\Sigma c$);

(b) calculating the sum of the normalized peak heights of the test polymer peak ($\Sigma s$);

(c) determining the amount of labeled peptide within the test polymer as per equation (2)

$$\left(1 - \frac{\sum_c}{\sum_s}\right) \times 100 \tag{2}$$

(d) calculating the slope of the line obtained for the percent labeled peptide versus time to determine the rate of synthesis of a particular polymer.

When only two time points are used to determine the rate of synthesis of a polymer, the rate can be expressed as:

$$\frac{\text{percent labeled peptide at time 2}}{\text{percent labeled peptide at time 1}} \quad (3)$$

The above method can be carried out for any number of biopolymers from a particular cell or tissue to provide information to establish a database which can be used for the analysis of complex biological systems or chemical reactions. For example, analysis of the rate of biopolymer synthesis and the fragment pattern produced by enzyme digestion of proteins or polypeptides can be used for the identification of a particular organism or for the identification of an unknown polymer.

In another aspect of the present invention, a method for determining the rate of degradation of a particular polymer in an organism, tissue, cell, or cell free synthesis system is provided. The method comprises enriching a polymer class within a cell, tissue or cell free system with polymer comprising one or more stable isotope labeled monomer probes using one of the methods described above. Enrichment is carried out for a period of time sufficient for the mass isotopically polymer pool to comprise a substantial portion total polymer pool. After a predetermined time period the mass isotopically labeled probe is removed from the cell culture medium or the reaction mixture and is replaced with a non-mass isotopically labeled form of the monomer. Samples are collected at two or more predetermined time points and the abundance of the monoisotopic and isotopomeric peaks are measured using equation (2) provided above. Typically the time interval between sample collection is of sufficient duration that at least one labeled component probe molecule is lost from a labeled polymer molecule. The slope of the function defining the percent of polymer labeled versus time is equal to the rate of degradation. If samples are taken at only two time points the rate of degradation is equal to the percent labeled peptide at time 2 versus the percent labeled peptide at time 1.

The percent relative abundance of monoisotopic and isotopomeric peaks can be corrected for formation of newly synthesized polymer during the time period polymer degradation is being determined. Generally, the correction is determined by a control reaction used to measure the rate of polymerization which is run concurrently with the test reaction. Usually, the control reaction is run using the same conditions as the test reaction with the exception that stable isotope labeled monomer is added to the control culture medium or reaction mixture at the time the label is removed from the test reaction. Samples are taken at the same time points after removal or addition of the labeled monomer probe. At time zero a control sample is collected and the abundance of monoisotopic and isotopomeric peaks for the polymers in a sample or a particular polymer or fragment thereof is determined. This value provides a relative baseline abundance for the monoisotopic and isotopomeric peaks prior to the addition of the labeled probe. The control reaction provides a measure of the relative amount of new polymer synthesized during the time period degradation is being measured.

Generally, samples are collected from the control reaction and the test reaction at predetermined time points. The relative abundances of the monoisotopic and isotopomeric peaks are determined for each sample. The proportion of new polymer synthesized is subtracted from the relative mass abundance determined for the test reaction at the same time point, and the percent enrichment of labeled polymer remaining at that time point is calculated by equation (4).

$$\left(1 - \frac{\text{corrected relative abundance polymer } T_n}{\text{relative abundance polymer } T_o}\right) \times 100 \quad (4)$$

The calculated percent enrichment at any time point following the removal of the labeled probe from the test reaction is subtracted from the percent enrichment at the time the label was removed, and the difference is equal to the rate of polymer degradation. As above, the rate of degradation of a number of biopolymer provides descriptors for a particular organism, tissue, cell or of a chemical reaction. The descriptors are stored in a database which is used to identify an unknown organism, tissue, cell, etc. The database can also be used to establish the particular physiologic state of an organism, tissue, cell or cell-free reaction.

In practicing the methods of the present invention to determine the rate of polymer synthesis and/or degradation, a biosystem database can be assembled. The database comprises stable isotope abundance information associated with various descriptors of the biological system. Biological systems can be described and defined in numerous ways. Generally, using an organism as an example of a complex biological system, the organism can be defined by, for example, its outward appearance, and by the organization of cells into particular organs and organ systems. In turn, the organ and organ systems can be defined by the cells which make up the organ. The cells in an organ can be described and characterized by, for example, their outward appearance as well as numerous other descriptors such as for example, membrane lipid components, cell surface, molecules, state of activation or differentiation; cytoplasmic and nuclear biopolymers, and the like.

Methods are well known to the skilled artisan for the determination of various cell descriptions. For example, cell surface markers or antigens can be used not only to define a particular cell type, but can also be used to determine the state differentiation and physiologic state of a cell. As a particular example, monoclonal antibodies directed to cell surface markers have been used to type or characterize various cell types in order to define the state of cellular differentiation or activation. Monoclonal antibodies have been used to distinguish white blood cell types, for example, T cells and B cells. Further these cells can be subdivided into helper T cells and suppressor T cells and the like. T cells can also be further characterized as activated or inactivated by the appearance of cell surface markers which can be detected by monoclonal antibodies, and the like.

Therefore, the database of the present invention can include any number of descriptors of a biological system. For example, descriptors can include, but are not limited to organism type, cell type, state of cellular differentiation, labeled monomer used to label the system, identification of biosphere, rate of incorporation or degradation of a biopolymer, method of biopolymer fragmentation, and the like. The database of the present invention is not meant to be limited by the descriptor of the biological system or by the method used to determine the descriptor. The combination of prior known methods of describing biological systems with the methods of the present invention provides a novel way to rapidly examine and understand regulatory processes within organisms and cells.

The present invention further provides a computer assisted method for correlating the relative abundance of monoisotopic and isotopomeric peaks obtained for a biopolymer fragment using a programmed computer comprising a processor, a data storage system, at least one input device and at least one output device with a database of descriptors described above. The method comprises generating input data comprising the relative abundance of isotopomeric and monoisotopic peaks for an unknown biopolymer fragment or the like; inputting the generated data into the programmed computer through one of the input devices; comparing, by means of the processor, the relative abundance data to a computer database of other biopolymers of known relative abundance data stored in the computer data storage system; selecting, using computer methods, analogous relative abundance data in the computer database; and outputting to at least one output device the selected analogous relative abundance data.

In practicing the present invention a cell or tissue is typically isolated and stimulated to respond to a stimulus. As described above, the rate of synthesis or degradation of any number of biopolymers isolated from the cell or tissue can be determined. The information collected for each biopolymer of the particular cell or tissue comprises a finite set or library of biopolymers characteristic of that cell or tissue. A particular biopolymer within that library can be characterized by, for example, its rate of synthesis or degradation within the cell or tissue in response to a given stimulus. In addition, each polymer member of the library can be defined by the labeled fragment pattern or "fingerprint" obtained when the parent polymer is fragmented. Each fragment is typically a certain size with or without a labeled monomer incorporated into the fragment. Comparison of the "fingerprint" of an unknown polymer sample with the database provides a rapid and convenient means to identify the unknown polymer.

Generally, in the practice of the method of the present invention, the following steps can be used to establish a database. A particular organism or collection of cells is selected. The organism can be either unicellular or multicellular. If a multicellular organism is selected, the cells can be either differentiated into a specialized tissue or undifferentiated. The selected cells can be isolated by any method, chosen primarily based on the characteristics of the organisms or type of cell selected. The isolated cells can then be grown in culture under conditions conducive to sustaining the viability of the isolated cells. Conditions for maintaining various organisms and cells, both differentiated and undifferentiated, are available in the art.

The organism or cells are cultured in vitro in the presence of a stable mass-isotopically labeled monomer of a polymer of interest. The labeled monomer is added to the culture medium and allowed to incorporate into newly synthesized polymer for a desired period of time. It is often preferred, as described above, that the culture medium be depleted of the particular unlabeled component prior to the addition of the labeled component probe.

After labeling, polymer or fragments thereof can be isolated as either purified polymer or as a mixture of a polymer class. The isolated polymer can then be further fragmented enzymatically, chemically, or by mechanical force resulting in destruction of the covalent primary structure of the polymer. In the practice of the rapid identification method of the present invention it is often desirable to process the polymers as minimally as possible prior to analyzing the mass spectrum of the polymer. Resultant fragments are then analyzed by a method which is capable of distinguishing the mass of the product. As provided above, mass spectrometric analysis is commonly used in the practice of the present invention.

The isolated fragments can themselves be further fragmented or disrupted, such as by, enzymatic, chemical or mechanical means to yield additional mass, charge. fragment ions detectable by mass spectrometric analysis. All data collected for each fragment can be reduced to digital representation that uniquely characterizes each fragment as a mass change set of values with an n-dimensional attribute qualifier. An attribute qualifier as used herein denotes a particular source of the polymer and can include, but is not limited to, species type, cell type, cell growth type, and the like. It should also be noted that each ratio for a mass/ion fragment produced by the disruption of the primary structure of a selected polymer also constitutes a unique set of attributes of the fragmented polymer. In addition to the unique identifier a quantitative measurement of each mass/ion fragment is also obtained. Collected database entries also contain a time attribute that represents either the interval of incorporation of the isotope-labeled component probe to provide a rate of polymer synthesis, or the interval of withdrawal from the isotope labeled component probe coupled with addition of the non-labeled component to provide a rate of polymer degradation.

A test sample comprising a collection of cells from an organism will be processed in the same manner as samples used to establish the database attributes. Any designated unknown parent-polymer can be fragmented as above and the resultant mass spectral data compared to the established database. Correlation with the database provides identification of the polymer of interest. Correlation of a number of specific polymer attributes of a number of polymers can provide identification of, for example, the unknown polymer, species type, cell type or physiologic state of a cell collection of interest.

As a particular example, the rate of β-actin synthesis in murine T cells activated to proliferate can be determined as described above. In determining the rate of synthesis stable isotope-labeled leucine and isoleucine are incorporated into the synthesized proteins. Proteins produced during labeling are isolated by two-dimensional gel electrophoresis. The β-actin protein is excised from the gel and the gel slice containing the protein fragmented by enzymatic digestion. Labeled leucine and isoleucine is incorporated into certain fragments produced by enzymatic digestion, depending on the protease used to fragment the protein. The fragment pattern of monoisotopic and isotopomeric peaks obtained for β-actin produces a fingerprint characteristic of β-actin that has been digested with a particular protease and isolated from proliferating T cells.

A similar population of proliferating cells can be labeled in the same manner and samples obtained at the same predetermined time points as used for β-actin above. The proteins can be separated in an identical manner and the protein spots excised from the gel and digested with the same proteases. The abundance of monoisotopic and isotopomeric peaks can then be determined for the fragments obtained from each spot and the abundances compared to the database constructed for activating proliferating murine T cells including that obtained for β-actin.

When it is desired to identify a particular polymer and the identity cannot be unambiguously determined by comparing the relative abundance data obtained for the polymer and fragments thereof, existing private or public databases can also be used based on the predicted masses of fragments which would be generated when the polymers of the database are fragmented in the same manner. The descriptors for various polymers isolated and characterized by the present invention can be compared with sequence libraries of the prior art to rapidly identify a specific unknown polymer. For example, the Genpept database the GenBank database (described in Burks et al., "GenBank: Current Status and Future Direction in *Method in Enzymology* 183:3 (1990)), EMBL data library (described in Kahn et al., "EMBL Data Library, *Methods in Enzymology* 183:23 (1990)), the Protein Sequence Database (described in Barker et al., "Protein Sequence Database," *Methods in Enzymology* 83:31 (1990)), Swiss-Prot protein sequence data bank (described in Bairoch, et al., "The Swiss-Prot protein sequence data bank, recent developments," *Nucl. Acids Res.* 21:3093-3096 (1993)), and PIR-International (described in "Index of the Protein Sequence Database of the International Association of Protein Sequence Databanks (PIR-International)" *Protein Seq. Data Amel.* 5:67-192 (1993)). Various other random genomic sequences tag databanks can also be used. If an identity still can not be confidently determined, the polymer can be identified using techniques available to the skilled artisan. These methods are particular for the polymer of interest and can include, but are not limited to tandem mass spectrometry, Edman degradation sequencing, or oligonucleotide sequencing using standard methods. It should be noted that once a polymer has been identified the attributes of the identified polymer can be added to the database with associated descriptors.

The following examples are offered by way of illustration, not by way of limitation.

EXAMPLE

Measuring the Rate of Protein Synthesis Using Stable Isotope Labeled Amino Acids The following example provides a description of the methods of the present invention for the measurement of the rate of protein synthesis. In one example, the rate of β-actin synthesis is determined in a mouse T cell line which has been stimulated to proliferate.

A. T-Cell Line Culture

Prior to beginning a labeling experiment and during the log growth phase, a mixture of proliferating T cells and irradiated Antigen Presenting Cells (APCs) were harvested into 50 ml polypropylene tubes. Any cells remaining stuck to the bottom of the tissue culture flask were removed by treating the cells with 0.5 M % EDTA in sterile saline for approximately 3 to 5 min. These cells were pooled with the cells in suspension and centrifuged at 150 xg for 6 min. After discarding the supernatant, the cells were reconstituted in leucine and isoleucine-free RPMI 1640 supplemented with 2 mM L-glutamine, 0.01 M HEPES, 1 mM sodium pyruvate. 100 U/ml penicillin, 100 µg/ml streptomycin, 1% fetal calf serum (RPMI-Leu$^-$/Ile$^-$). The cells were centrifuged at 150 xg for 6 min, the supernatant was discarded. The cells were reconstituted in 10 ml of RPMI-Leu$^-$/Ile$^-$, and placed at 37° C./5% $CO_2$ for 30 min to deplete the cells of their endogenous pool of unlabeled leucine and isoleucine. To make tissue culture media with stable amino acid isotopes, RPMI-Leu$^-$/Ile$^-$ was supplemented with 25 mg/L of $^{15}$N-Leucine (98 atom %, Sigma-Aldrich) and 25 mg/L of $^{15}$N-Isoleucine (98 atom %, Sigma-Aldrich) or with $^{15}$N-Lysine (99 atom %, MassTrace, Inc., Woburn, Mass.) to make RPMI-Leu*/Ile*. After the 30 min incubation in RPMI-Leu$^-$/Ile$^-$, the cells were centrifuged at 150 xg for 6 min, the supernatant was discarded, and the cells were reconstituted in RPMI-Leu*/Ile*. The cells were incubated at 37° C./5% $CO_2$ for the desired amount of time, harvested as described above and centrifuged at 150 xg for 6 min. The supernatant was discarded, and the cells were reconstituted in 3.5 ml of RPMI-Leu$^-$/Ile$^-$ and transferred to a 15 ml conical polypropylene tube. 3.5 ml of lymphocyte separation medium (Organon Teknika) was underlayed below the cell suspension and the tubes were centrifuged at 400 xg for 15 min. Live T cells were harvested from the interface between the culture media and the separation medium, and placed in 10 ml of RPMI-Leu$^-$/Ile$^-$. The cells were centrifuged at 150 xg for 6 min, the supernatant was discarded, the cells were washed once more in RPMI-Leu$^-$/Ile$^-$. The cells were then reconstituted in RPMI-Leu$^-$/Ile$^-$ and aliquoted into 1.5 ml siliconized microcentrifuge tubes.

B. Mammalian Cell Solubilization

Cells were centrifuged lightly in a microcentrifuge and the supernatant was discarded. The tubes were gently tapped to loosen the cell pellet. All subsequent steps were performed in a 4° C. chamber. A boiling solution of 0.3% SDS, 1% β-mercaptoethanol, and 50 mM Tris-HCl, pH 8.0 was added to the loosened cell pellet, and 0.1 volumes (1:10) of (1 mg/ml) DNase I, 500 µg/ml RNase A, 50 mM $MgCl_2$, 50 mM Tris-HCl, pH 7.0 was added immediately. The tubes were vortexed for a few seconds and placed in boiling water for 1 minute. Once removed from the boiling water, the tubes were vortexed vigorously, and microcentrifuged on high for 5 to 10 seconds. The tubes were placed on ice and capped with pre-prepared caps from 1.5 ml microcentrifuge tubes that had been cut and a small hole made through the cap with a needle. Samples were frozen by immersing the tubes into a liquid nitrogen bath. Samples were immediately centrifuge lyophilized (SpeedVac, Savant) for a minimum of 2 hours and up to 8 hours. After lyophilization, the samples were redissolved to the original volume (to maintain SDS concentration) with 9.95 M urea, 4.0% Nonidet P-40, 2% pH 6-8 ampholytes (Pharmacia Biotech), and 100 mM dithiothreitol. Tubes were placed in a 37° C. water-bath for 3 minutes, vortexed vigorously and centrifuged on high for 2 minutes in a microcentrifuge. The liquid was transferred to a new siliconized 1.5 ml microcentrifuge tube and the samples were stored at −80° C. until further use.

C. Yeast Cell Labeling and Solubilization

Yeast cells, *Saccharomyces cerevisiae*, were grown in complete medium. The cells were harvested and washed in leucine and isoleucine-free complete medium. The cells were collected and the supernatant discarded. Cells were depleted of their endogenous pool of labeled leucine and isoleucine by culturing the cells in complete medium free of leucine and isoleucine for 30 minutes. After depletion the cells were washed and resuspended in complete culture medium with stable amino acid isotopes, 25 mg/L of $^{15}$N-leucine (98 atom % Sigma-Aldrich) and 25 mg/L of $^{15}$N-isoleucine (98 atom % Sigma-Aldrich). The cells were labeled for twenty-four hours after which cells were centrifuged lightly in a microcentrifuge and the supernatant was discarded. The tubes were gently tapped to loosen the cell pellet. The cells were resuspended in 100 ml of lysis solution (20 mM Tris-HCl, pH 7.6, 10 mM NaF, 10 mM sodium chloride, 0.5 mM EDTA, 0.1% deoxycholate) to which a final concentration of (1mM 4-(2-aminoethyl) benzenesulfonyl fluoride (AEBSF), 1 mg/ml leupeptin, 1 mg/ml pepstatin, 10 mg/ml N-tosyl-L-phenylalanine chloramethyl ketone (TPCK), and 10 mg/ml soybean trypsin inhibitor) was added just prior to use.

Resuspended cells were transferred to a 1.5 ml screw-cap tube containing 0.28 g of 0.5 mm glass beads, and vortexed vigorously for 2 minutes. The cell/glass bead mixture was centrifuged at 5000 xg for 10 seconds at 4° C. The liquid was withdrawn and transferred to prechilled 1.5 ml tubes containing 0.1 volumes (about 7 ml) of DNase/RNase mixture (1.0 mg/ml DNase I, 0.5 mg/ml RNase A, 50 mM $MgCl_2$, 50 mM Tris-HCl, pH 7.0). The mixture was incubated on ice for 2 minutes. Typically about 70 ml out of 100 ml was recovered. An equal volume of 2× solubilization buffer (the 2× solution contains 0.6% SDS, 2% β-mercaptoethanol, 0.1 M Tris-HCl, pH 8.0) was added, and the tubes were plunged into boiling water and incubated for 1 minute. All subsequent steps in the sample preparation were identical to those described above for mammalian cell preparation.

D. Two-Dimensional Gel Electrophoresis

Soluble proteins were run in the first dimension using a commercial flatbed electrophoresis system (Multiphor II, Pharmacia Biotech). Immobilized polyacrylamide gels (IPG) dry strips with non-linear pH 3.0-10.0 gradients (Amersham-Pharmacia Biotech) were used for the first dimension. 10-60 μg of protein from whole cell lysate was mixed with IPG strip rehydration buffer (8 M urea, 2% Nonidet P40, 10 mM dithiothreitol), and 250-380 μl of solution was added to individual lanes of a IPG strip rehydration tray (Amersham-Pharmacia Biotech). The strips were allowed to rehydrate at room temperature for 1 to 2 hours, during which time 70%-100% of the buffer/sample solution was taken up into the gel. IEF electrode strips were cut into 35 mm lengths, placed on a glass plate, and wetted with 100 μl of deionized water (Milli-Q, Millipore). A moist electrode strip was placed at each end of the IPG strip so that the electrode strip made contact with the gel. The anode electrode was placed at the acidic end of the IPG strip, and the cathode electrode was placed at the basic end. The IPG strips were completely covered with mineral oil, and the safety lid was placed on the apparatus. The samples were run at 300V/10 mA/5W for 2 hours, then ramped to 3500V/10 mA/5W over a period of three hours, then kept at 3500V/10 mA/5W for 15 to 19 hours (for a total of 40-70 kVH).

The IPG strips were removed from the apparatus, and placed in a reequilibration tray made up of individual lanes containing 4 ml of 2% w/v dithiothreitol in 2% w/v SDS, 6 M urea, 30% w/v glycerol, 0.05M Tris HCl (pH 6.8). The IPG strips were incubated in this solution for 8 min., the solution was discarded, and 4 ml of 2.5% iodoacetamide in 2% w/v SDS, 6M urea, 30% w/v glycerol, 0.05M Tris HCl (pH6.8) with a touch of bromophenol blue, was added for 4 min. The iodoacetamide solution was discarded, and the strips were transferred and apposed to 10% polyacrylamide second dimension gels.

The polyacrylamide gels were made by pouring in a casting stand a solution of 10% acrylamide/2.67% N,N'-diacryloyl piperazine (PDA), 0.375 M Tris base/HCl (pH 8.8), 0.1% w/v SDS, 0.05% w/v ammonium persulfate, and 0.05% TEMED, in deionized water (Milli-Q, Millipore). Gel dimensions were 205 mm×200 mm×1 mm (height×width×thickness), with a 25 mm space between the top of the gel, and the top of the glass plate sandwich. Once poured, the gels were overlayed with 2.5 ml of water-saturated 2-butanol, covered, and allowed to set at room temperature overnight. The next day the gels were removed fro m the casting stand, the outside plates were rinsed free of extra gel material, and the gels were placed at 4° C. for a minimum of two days prior to using them.

On days when the second dimension was n, the outside glass plates were rinsed once again and reservoir buffer (0.25 M Tris Base, 1.92 M glycine, 1% w/v SDS) was added to the top of the gel to insure that the gel/glass plate sandwich did not leak.

The apparatus used to run second dimension gels was a non-commercial apparatus from Oxford Glycosciences Inc. The apparatus was essentially a large plexi-glass tank with tank buffer circulating through a series of coiled tubing immersed in water from a circulating water bath. The tank buffer intake was at the bottom of the lower reservoir. Tank buffer was drawn into a series of immersed coiled tubing by an aquarium pump, and was circulated via glass tubes through the upper reservoir chamber, then returned to the lower reservoir via perforated glass tubing. The tank buffer was pre-chilled to 8° C. prior to running the second dimension.

The IPG strips were apposed to the second dimension gels and were immediately run at 50 mA constant/500V/85W for 20 min., followed by 200 mA constant/500V/85W until the bromophenol blue line was 10-15 mm from the bottom of the gel. Once the second dimension run was completed, the glass plates were opened up, the gels were quickly rinsed with distilled water. After rinsing the IPG strips were removed and discarded, and the gels were transferred into fixative prior to staining.

E. Silver Staining

Two-dimensional polyacrylamide gels were fixed for 9 to 12 hours in 40% ethanol, 10% acetic acid. After 9 to 12 hours of fixation, gels were transferred to 10 to 30% ethanol for 15 min., then washed three times for 5 min. in distilled water ($dH_2O$). Gels were sensitized with 150 ml of fresh 0.2 g/L anhydrous sodium thiosulfate for 1.5 min, then washed three times for 30 sec in distilled water ($dH_2O$). The gels were treated with 150 ml of 2.0 g/L silver nitrate in $dH_2O$. After 25 minutes the gels were washed twice with approximately 2-3 liters of $dH_2O$ for 30 to 60 sec, and 150 ml of developing solution (60 g/L sodium carbonate, 20 ml/L of the sodium thiosulfate solution used during sensitization, and 500 ml/L 37% formaldehyde, in $dH_2O$) was added until the desired level of staining was achieved. Development was stopped by discarding the developing solution and adding 6% acetic acid in $dH_2O$ for 10 min. The gels were then washed a minimum of three times in $dH_2O$. Protein spots were excised from the wet gels, or from gels dried between cellophane membrane backing sheets (Bio Rad).

F. Protein Digestion for Tandem Mass Spectrographic Analysis.

A portion of gel containing a protein spot was excised from silver stained 2D-polyacrylamide gels and placed in 0.8 ml or 1.5 ml microcentrifuge tubes and the tubes were filled with $dH_2O$. The water was discarded and 10-60 μl of 100% acetonitrile was added to the tubes for 15 min. The acetonitrile was removed, and the gel pieces were dried by centrifugal lyophilization (Speed-Vac, Savant). Gel pieces were reswollen in a pre-chilled (4° C.) solution containing 100 mM ammonium bicarbonate, 5 mM calcium chloride, and 12.5 ng/ml sequence grade porcine trypsin (Promega) and placed on ice for 45 min. A sufficient volume of this solution was added to cover the gel pieces. The tubes were periodically checked during the 45 min incubation, and more solution was added if the gel pieces had soaked up all of the available liquid.

After 45 min., the remaining supernatant was discarded and the gel pieces were covered with the ammonium bicarbonate—calcium chloride solution without trypsin, and incubated overnight at 37° C. The following day the supernatant was saved, and the peptides were extracted by treating the gel pieces with 20 mM ammonium bicarbonate for 20 min at room temperature. The supernatant was pooled with the supernatant from the overnight incubation, and the peptides were further extracted with 3 changes of 50% acetonitrile, 5% formic acid in $dH_2O$ for 20 min. per change. The supernatants were pooled for each gel piece and totally dried down by centrifugal lyophilization (Speed-Vac, Savant). Dried samples were reconstituted with 5% formic acid in $dH_2O$ and used immediately, or stored at −80° C.

G. Protein Digestion for Matrix-Assisted Laser Desorption-Ionization (MALDI) Mass Spectrographic Analysis Protein digestion of samples to be analyzed by MALDI analysis were digested as above for tandem Mass Spectrographic Analysis except that gel pieces were first destained for 5 min. in 800 μl of a 1:1 working solution of 30 mM potassium ferricyanide and 100 mM sodium thiosulphate, and washed four times with $dH_2O$ prior to the addition of acetonitrile.

H. Microcolumn High Performance Liquid Chromatography

Microspray column chromatography was accomplished using the methods described in Gatlin et al. (incorporated herein by reference). Briefly, a length of 365 OD×100 ID fused silica was pulled to a tip of approximately 5 mm using a laser needle puller. This was packed to a length of 9 cm with PerSeptive Biosystems POROS 10 R2 (Framingham, Mass.), a 10 mm reversed-phase packing material. This column was mounted on a custom designed electrospray ionization platform on the Finnigan MAT LCQ (San Jose, Calif.). An aliquot of 5-15 μl was loaded onto the column using a helium pressurized bomb. HPLC was performed using a 1100 binary solvent pump (Hewlett-Packard, Palo Alto, Calif.). The flow from the pump was reduced from 150 ml/min to 1 ml/min using a "splitting-tee" and a length of restriction tubing made from fused-silica. The mobile phases used for gradient elution consisted of (A) 0.5% acetic acid and (B) acetonitrile/water 80:20 (v/v) containing 0.5% acetic acid. The gradient was linear from 2-60% B over 30 minutes.

I. Automated Tandem Mass Spectrometry on the LCQ

Tandem mass spectra were acquired on the Finnigan MAT LCQ electrospray ionization ion trap mass spectrometer through an instrument control algorithm pre-programmed by the instrument manufacturer. A unit mass resolution scan over an m/z range of 400-1400 was acquired. If an ion was present in the scan above an ion abundance threshold of 100,000 counts, then a high resolution Zoom scan and an MS/MS scan were acquired of this ion. The Zoom scan performs a 10 amu wide, high resolution scan centered on the selected ion. This scan was used to resolve the isotope peaks. The MS/MS scan range was set by assuming a doubly-charged parent ion. However, this did not prevent the acquisition of tandem mass spectra for triply-charged peptides. Precursor ions were selected within a mass window of 3 amu. A collision energy of 35% was used.

Figure 3A:
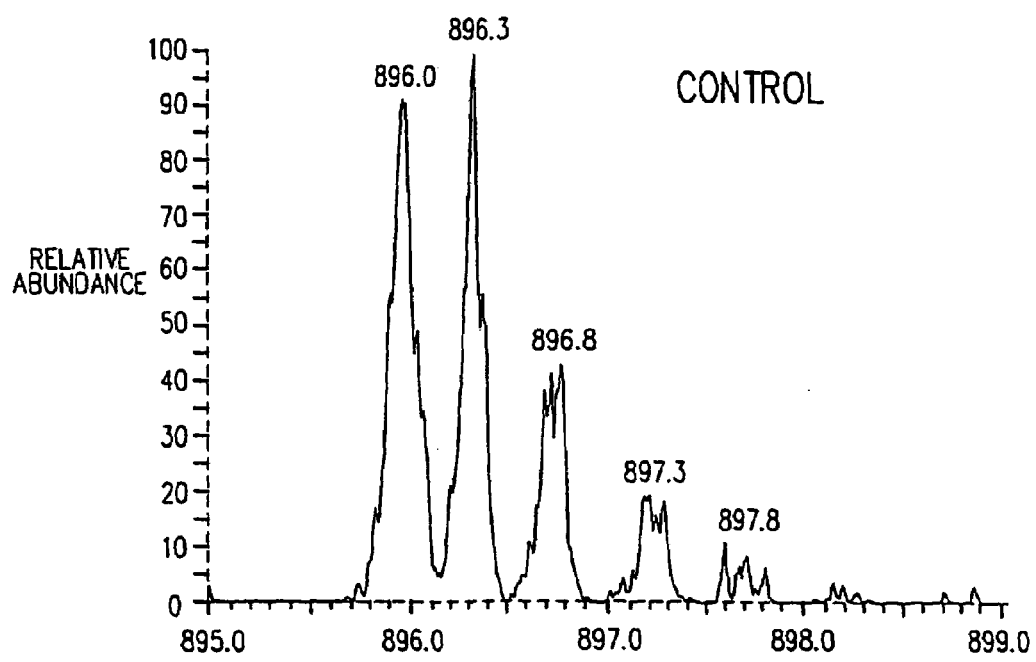

As depicted in FIGS. 3A-3C for a peptide from the β-actin spot, incorporation of $^{15}N$-leucine and $^{15}N$-isoleucine labeled amino acids into the protein resulted in an increase in the relative abundance of certain isotopomeric peaks above those present in the control spectra, and in an increase in the absolute number of isotopomeric peaks. Calculation of the fraction of newly synthesized protein was accomplished by comparing the sum of the relative abundances of each mass peak of the control sample, to that of the sum of the relative abundances of each mass peak of the sample grown in the presence of labeled amino acids using equation 5.

The relative extent of protein synthesis at several time points was calculated for different peptides from individual proteins to determine the range of values found when different peptides from one protein were also analyzed. It can be appreciated that analysis of peptide mass spectra is complicated when more than one probe is incorporated into the peptide. Using a peptide which incorporates three probes as an example, it is apparent from the distribution of isotopomeric peaks that peptides exist that have only incorporated probe at two of the three possible amino acid locations (FIG. 3). This phenomenon is likely a result of incomplete depletion of the unlabeled amino acid pool. Since rates of protein synthesis were determined using a number of time points, partial depletion of the amino acid pool prior to adding probe would not significantly affect rate determinations. Specifically, the extent of depletion at the start of the experiment would be expected to be equal for all samples within a time-course. In order to simplify the quantitation of labeled amino acids into proteins, stably labeled lysine or arginine were used as a probe. These amino acids were chosen because the majority of peptides cleaved by trypsin will contain only one of either of these amino acids, since trypsin generally cleaves proteins after an arginine or a lysine residue.

There is no exchange of labeled nitrogen moieties between peptides during the digestion procedure, since trypsin autodigestion peptides from unlabeled samples have virtually identical isotope peak distributions as those from labeled samples.

J. MS/MS Database Searching

A protein sequence database was searched directly with tandem mass spectra (Yates, *Electrophoresis* 19:893-900 (1998), incorporated herein by reference in its entirety) using the computer program, SEQUEST12. A mouse subset of the OWL non-redundant protein database (Bleasby et al., *Nucleic Acids Res.* 22:3574-3577 (1994), incorporated herein by reference) was used for the searches.

K. Calculation of the Extent of Amino Acid Incorporation

In order to calculate the extent of amino acid incorporation into newly synthesized proteins, the sum of the relative peak heights of the monoisotopic and all discernible isotopomeric peaks (ion peak distribution) was calculated for peptides from unlabeled proteins (control samples), and compared to the ion peak distribution of samples from cells grown in the presence of labeled amino acids (test samples). For each peptide analyzed, the monoisotopic peak was normalized to 100%, and all the other peaks in the distribution were normalized with respect to the monoisotopic peak. The sum of the normalized values for all peaks within the ion peak distribution was calculated for both the control and test samples, and the percent of the peptide present in the test sample which contained stable isotopes was calculated as per equation 5;

$$\left(1 - \frac{\sum_c}{\sum_s}\right) \times 100 \qquad (5)$$

where Σc is the sum of the normalized ion peak distribution for a peptide from a control sample, and Σs is the sum of the normalized ion peak distribution for a peptide from a sample grown in the presence of labeled amino acids.

When only two time points have been collected, the ratio of the two values can be determined using equation 6.

$$\frac{\text{percent labeled peptide at time 2}}{\text{percent labeled peptide at time 1}} \qquad (6)$$

The slope of the line defining the percent labeled isotope versus the time after labeled isotope removal ($T_0$) provides the rate of synthesis of a particular polymer.

L. Calculation of the Rate of Polymer Degradation

To calculate the rate of degradation of polymer proteins, the sum of the relative peak heights of the monoisotopic and all discernible isotopomeric peaks (ion peak distribution) was calculated for peptides from unlabeled proteins (control samples), and compared to the ion peak distribution of samples from cells grown in the presence of labeled amino acids (test samples). For each peptide analyzed, the monoisotopic peak was normalized to 100%, and all the other peaks in the distribution were normalized with respect to the monoisotopic peak. The sum of the normalized values for all peaks within the ion peak distribution was calculated for both the control and test samples, and the percent of the peptide present in the test sample which contained stable isotopes was calculated as above using equation 5. The percent labeled values calculated was then plotted in relation to the time the sample had been collected following removal of the stable isotope label. The slope of the line was used to determine the rate of degradation.

The peptide shown in FIGS. 3A-3C contains one leucine and two isoleucine residues. If every newly synthesized β-actin molecule contained only labeled leucine and isoleucine, then one would have expected the peptide in FIG. 3C to show a substantial increase in the isotopomeric peaks at 897.4 and 897.8. The relative abundance of these two mass peaks were significantly increased over that found in the control and 24 hour samples. However, a relative increase in the abundance of the peaks at 896.5 and 896.9 was also detected compared to the monoisotopic peak at 896.0, suggesting that some peptides incorporated probe at only one or two of the three possible amino acid locations. Incomplete depletion of the unlabeled amino acid pool or loss of the $^{15}N$ label due to transamination of leucine or isoleucine during cell culture (Matthews et al., Science 214:1129-1131, 1981) (see below) may account for this result. Since rates of protein synthesis would be determined from a number of time points, partial depletion of the amino acid pool would not be expected to significantly affect rate determinations since the extent of depletion at the start of the experiment will be similar for all samples within a time-course.

The fraction of newly synthesized protein was calculated at several time points for different peptides from β-actin to determine the variability in experimental values between peptides from a single protein (Table 2). For the technique to be robust, peptides from one protein should show similar levels of labeled amino acid substitution. In addition, calculated ratios of percent substitution should be independent of the number of potential amino acid substitution sites in the peptide (i.e. the number of leucine and isoleucine per peptide for the data presented in Table 2). Calculated values of percent substitution at 24 and 53 hours were similar for all peptides analyzed. Only peptide 1954.1, a peptide with a charge of +3, showed values (significantly) deviating from the others at the 24 hour time point. The average ratio of the calculated values at 53 hours versus 24 hours for the 7 peptides known to contain at least 1 leucine or isoleucine was 1.62+0.15 (standard deviation equal to 9% of the mean). The average value for the ratio for the 2 peptides with one probe was 1.66, 1.56 for the two peptides with 2 probes, and 1.62 for the three peptides with 3 probes. Thus, calculated values of the ratios are independent of the number of probes within the peptides.

TABLE 2

Determination of the extent of labeled amino acid incorporation in peptides from β-actin using ion-trap MS.

| PEPTIDE | MW | SUM OF ISOTOPE PEAK HEIGHTS* | | | % SYNTHESIZED | | RATIO |
| --- | --- | --- | --- | --- | --- | --- | --- |
| | | CONTROL | 24 HRS. | 53 HRS. | 24 HRS. | 53 HRS. | 53 H/24 H |
| AVFPSIVGR (SEQ ID NO. 3) | 945.5 | 174.5 + 10.2 | 242.8 + 18.8 | 343.5 + 47.4 | 28.1 | 49.2 | 1.75 |
| DLTDYLMK (SEQ ID NO. 4) | 1014.5 | 188.8 + 21.8 | 281.7 + 22.2 | 397.0 + 89.0 | 33.0 | 52.4 | 1.59 |
| AVFPSIVGRPR (SEQ ID NO. 5) | 1198.7 | 211.0 + 21.3 | 317.1 + 44.8 | 444.9 + 70.8 | 33.5 | 52.6 | 1.57 |
| SYELPDGQVITIGNER (SEQ ID NO. 1) | 1790.9 | 296.6 + 34.6 | 436.1 + 37.2 | 703.1 + 97.6 | 32.0 | 57.8 | 1.81 |
| DDDIAALVVDNGSGMCK (SEQ ID NO. 7) | 1838** | 310.2 + 36.0 | 466.0 + 118.0 | 633.6 + 120.4 | 33.4 | 51.0 | 1.53 |
| VAPEEHPVLLTEAPLNPK (SEQ ID NO. 8) | 1954.1# | 460.9 + 76.2 | 797.7 + 253.8 | 1093.9 + 256 | 42.2 | 57.9 | 1.37 |
| DLYGNVVLSGGFTMFPGIADR (SEQ ID NO. 2) | 2230.5 | 391.5 + 79.7 | 606.0 + 64.0 | 974.6 + 136.0 | 35.4 | 59.8 | 1.69 |
| AGFAGDDAPR (SEQ ID NO. 10) | 976.5 | 196.8 + 27.5 | 257.7 + 37.1 | 402.2 + 59.2 | 23.6 | 51.1 | 2.17 |
| GYSFTTTAER (SEQ ID NO. 11) | 1133.2 | 237.6 + 32.0 | 352.2 + 46.9 | 340.6 + 70.6 | 32.5 | 30.2 | 0.93 |
| VATVSLPR⁻ (SEQ ID NO. 12) | 842 | 169.6 + 11.3 | 152.4 + 8.2 | 153.5 + 6.6 | 0 | 0 | 0 |

*All peaks within the isotope peak spectra were normalized using the monoisotopic peak set at 100.
**Data for this peptide was pooled data from the peptide appearing in several modified forms (MW's of 1823.8, 1838.6, and 1855.8). All modified forms were confirmed using MS/MS fragmentation spectra.
This peptide had a +3 charge. All other peptides analyzed had a +2 charge.
⁻Peptide from porcine trypsin.

TABLE 3

Determination of the extent of labeled amino acid incorporation in peptides from β-actin using MALDI MS.

| PEPTIDE | MW | SUM OF ISOTOPE PEAK HEIGHTS* | | | % SYNTHESIZED | | RATIO |
| --- | --- | --- | --- | --- | --- | --- | --- |
| | | CONTROL | 24 HRS. | 53 HRS. | 24 HRS. | 53 HRS. | 53 H/24 H |
| LDLAGR (SEQ ID NO. 13) | 644.4 | 174.3 + 16.3 | 230.0 + 25.8 | 314.0 + 11.9 | 24.2 | 44.5 | 1.84 |
| IIAPPER (SEQ ID NO. 14) | 795.5 | 195.4 + 19.1 | 254.4 + 24.1 | 394.3 + 71.2 | 23.2 | 50.4 | 2.17 |

TABLE 3-continued

Determination of the extent of labeled amino acid incorporation in peptides from β-actin using MALDI MS.

| PEPTIDE | MW | SUM OF ISOTOPE PEAK HEIGHTS* | | | % SYNTHESIZED | | RATIO |
| --- | --- | --- | --- | --- | --- | --- | --- |
| | | CONTROL | 24 HRS. | 53 HRS. | 24 HRS. | 53 HRS. | 53 H/24 H |
| AVFPSIVGR (SEQ ID NO. 3) | 945.5 | 191.4 + 13.1 | 242.7 + 20.8 | 344.4 + 27.0 | 21.1 | 44.4 | 2.10 |
| QEYDESGPSIVHR (SEQ ID NO. 15) | 1516.7 | 273.6 + 18.9 | 347.8 + 51.8 | 493.4 + 97.9 | 21.3 | 44.5 | 2.09 |
| SYELPDGQVITIGNER (SEQ ID NO. 1) | 1790.9 | 284.0 + 14.7 | 455.8 + 39.4 | 648.9 + 74.5 | 37.7 | 56.2 | 1.49 |
| VAPEEHPVLLTEAPLNPK (SEQ ID NO. 8) | 1954.1 | 327.6 + 39.4 | 383.4 + 76.7 | 673.8 + 91.3 | (14.5) | 51.2 | (3.53) |
| DLYANTVLSGGTTMYPGIADR (SEQ ID NO. 2) | 2215.1 | 438.3 + 43.0 | 755.0 + 127 | ND | 41.9 | — | — |
| AGFAGDDAPR (SEQ ID NO. 10) | 976.5 | 203.1 + 14.4 | 251.1 + 29.5 | 329.5 + 25.0 | 19.1 | 38.4 | 2.01 |
| GYSFTTTAER (SEQ ID NO. 11) | 1133.2 | 223.6 + 14.4 | 241.0 + 20.3 | 278.7 + 16.3 | 7.2 | 19.8 | 2.75 |
| VATVSLPR** (SEQ ID NO. 12) | 842 | 206.2 + 12.2 | 185.4 + 12.4 | 179.5 + 10.3 | 0 | 0 | — |

*All peaks within the isotope peak spectra were normalized using the monoisotopic peak set at 100.
**Peptide from porcine trypsin.
ND No data available

TABLE 4

Determination of percent substitution levels using different stable isotope probes

| PEPTIDE | MW | % SYNTHESIZED AT 24 HRS. | |
| --- | --- | --- | --- |
| | | $^{15}$N-LEUCINE/ ISOLEUCINE | $^{15}$N-LYSINE |
| LDLAGR (SEQ ID NO. 13) | 644.4 | 24.2 | 0* |
| IIAPPER (SEQ ID NO. 14) | 795.5 | 23.2 | 0 |
| AVFPSIVGR (SEQ ID NO. 3) | 945.5 | 21.1 | 0 |
| QEYDESGPSIVHR (SEQ ID NO. 15) | 1516.7 | 21.3 | 0 |
| SYELPDGQVITIGNER (SEQ ID NO. 1) | 1790.9 | 37.7 | 5.7 |
| VAPEEHPVLLTEAPLNPK (SEQ ID NO. 8) | 1954.1 | (14.5) | 29.2 |
| DLYANTVLSGGTTMYPGIADR (SEQ ID NO. 2) | 2215.1 | 41.9 | 0 |
| AGFAGDDAPR (SEQ ID NO. 10) | 976.5 | 19.1 | 0 |
| GYSFTTTAER (SEQ ID NO. 11) | 1133.2 | 7.2 | 0 |

*For all values presented as 0, the sum of the peak heights for the control isotope spectra was greater than the sum of the peak heights for the isotope spectra of the 24 hour sample.

Exchange of labeled nitrogen moieties between peptides did not appear to occur during the digestion procedure since trypsin autodigestion peptides from unlabeled samples had virtually identical isotope peak distributions as those from labeled samples (Table 2). At the bottom of Table 2 data was also included from two peptides which were identified on the basis of collision-induced dissociation (CID) spectra Although these peptides do not appear to contain any leucine or isoleucine based on CID data, they showed mass isotope spectra suggesting stable isotope incorporation.

The branched amino acids leucine, isoleucine and valine are known to undergo transamination reactions (Matthews et al., Science 214:1129-1131, 1981). During the reaction, the amino terminus nitrogen from these amino acids can be transferred to a glutamic acid. Peptide 1133 contains 1 glutamic acid residue, and transamination may explain stable isotope incorporation in this peptide. The metabolic labeling of peptide 976.5 AGFAGDDAPR (SEQ ID NO. 10), was unexpected, as the arginine residue found in human actin has been reported to be converted to a leucine residue in mouse melanoma cells (Sadano et al., J. Biol. Chem. 263:15868-15871, 1988). However, if that were the case, the peptide would no longer have a MW of 976.5, since it would not be cleaved at the same location by trypsin. It is possible that one of the aspartic acids (MW 115.0) may be substituted with a leucine or isoleucine (MW 113.0) in the cell line used. In order to contravene the issue of potential loss of the label due to transamination, the mouse T-cell line can be cultured using $^{15}$N-lysine substituted amino acids (see Table 4).

In order to decrease sample analysis time, tryptic digests of mouse actin were also analyzed on a matrix-assisted laser desorption ionization (MALDI) time-of-flight mass spectrometer. Using MALDI, each sample can be analyzed in 2 to 5 min., compared to the 30-40 mm. necessary using liquid chromatography and an ion-trap MS.

The peptides giving strong signals using MALDI were similar to those identified using ion-trap MS (Table 3). However, average substitution values calculated for peptides analyzed using MALDI were consistently lower than those calculated from ion-trap MS experiments, especially at the 24 hour time point (Table 3). This resulted in calculated ratios (53h/24h) of 1.94±0.28 (mean±SD) from MALDI data versus 1.62±0.15 for ion-trap data. These results were not attributable to differences in substitution levels between cells from different growth experiments, as % substitution values for identical samples run on ion-trap MS or MALDI gave similar results to pooled data.

Since trypsin generally cleaves proteins after an arginine or a lysine residue, using $^{15}$N-lysine-as a probe will result in certain peptides containing only one labeled residue. Calculated % substitution values for the only lysine-containing a peptide showing a strong spectra were nearly identical to values calculated when leucine and isoleucine were used as probes (Table 4). In addition, all arginine containing peptides (no lysine) had isotope spectra similar to those found in control samples. This suggests that transamination of leucine and isoleucine is likely responsible for the observations discussed using the ion-trap methodology.

The theoretical distribution of isotope peaks for any peptide for which the amino acid sequence or elemental composition is known can be calculated using a set of mathematical formulas (Beynon, In Mass Spectrometry and its applications to organic chemistry, Elsevier Publishing Co., New York, p. 294-301, 1960; McCloskey, *Meth. Enzymol.* 193:882-886, 1990), or by using computer programs such as MS-Isotope (UCSF Mass Spectrometry Facility's MS-Isotope program can be found at the University of California San Francisco ProteinProspector website). For different peptides from control samples, the relative distributions of isotope peaks determined experimentally using MS-zoom scans or MALDI was compared to the theoretical distribution determined by the computer program MS-Isotope. Isotope peak distributions calculated from ion-trap MS data were similar to theoretical distributions for most peptides studied which had mass/charge values of +2 on the MS/MS (Table 5). On average, MS-Zoom values were 1.08 times higher than theoretical values, while MALDI values were 1.14 times higher than theoretical values. Since the discrepancies between the ratios (53H/24H) determined from ion-trap and MALDI were potentially due to differences in control isotope peak spectra alone, % substitution levels were calculated using theoretical isotope peak spectra for both ion-trap and MALDI data. Using theoretical control spectra and experimental spectra for the 24 hours and 53 hours time-points, calculated ratios for ion-trap MS were 1.65±0.10, compared to 1.57±0.12 for MALDI. Thus, it may be possible to use theoretical distributions of isotope peaks for calculations of substitution levels, rather than analyzing multiple control samples.

When analyzing MS/MS or MALDI spectral data from a peptide mixture derived from a spot on a 2D gel, it may not always possible to determine whether a "peptide" belongs to a protein which co-migrates to the same area on the 2D gel, or whether it might be a modified form of a peptide that was not recognized by analytical programs such as SEQUEST (Eng et al., *J. Am. Soc. Mass. Spectrom.* 5:976-989 (1994). In the initial time-course studies of cells metabolically labeled with stable amino acids, spots individually cut from 2D gels of known proteins such as actin, p60, and hsp70. For each of these proteins, a number of peptides were matched to the putative proteins using MS/MS and the SEQUEST program. However, a number of unmatched peptides were found whose isotopic spectra suggested stable isotope incorporation during the time-course. Since trypsin autolysis peptides or peptides belonging to keratin did not show stable isotope incorporation, unmatched peptides were either derived from a co-migrating protein, or were a modified form of a peptide.

To test whether unmatched peptides were modified peptides from the known protein, the masses of the peptides and the identity of the protein analyzed were entered into EXPASY's FindMod (Find Modification) tool found at the Expert Protein Analysis System of the Swiss Institute of Bioinformatics, a proteomics server website. The program gives a number of possible modified peptides based on the mass of the peptide entered. Using MS/MS data, the identity of the peptide many times could be determined. For example, peptide DLTDYLMK (SEQ ID NO. 4) (MW 998.5) was found to have an oxidized methionine residue and a MW of 1014.5 (Table 2). In addition to the presence of a carboxyamidomethyl cysteine (+58) formed when the first dimension strip was treated with iodoacetamide, peptide DDDIAALV-VDNGSGMCK (SEQ ID NO. 7) (MW 1722.8) was found to be acetylated (+42) at the N-terminus, while the methionine residue was either unoxidized, singly (+16), or doubly (+32) oxidized giving experimental MW's of 1823.8, 1838.6, and 1855.6. Thus, the stable isotope metabolic labeling technique was found to be useful in helping to select peptides from MS scans which may potentially be modified.

Although the foregoing invention has been described in some detail by way of illustration and example for purposes of clarity of understanding, it will be obvious that certain changes and modifications may be practiced within the scope of the appended claims.

TABLE 5

Comparison of experimentally determined control isotope spectra to theoretical values

| PEPTIDE | CONTROL/ION-TRAP | CONTROL/MALDI | CONTROL/MS-ISOTOPE | RATIO/ION-TRAP | RATIO/MALDI |
|---|---|---|---|---|---|
| 644.4 | — | 174.3 | 143.3 | — | 1.44 |
| 795.5 | — | 195.4 | 159.4 | — | 1.60 |
| 945.6 | 174.5 | 191.4 | 175.8 | 1.77 | 1.78 |
| 976.5 | 196.8 | 203.1 | 172.0 | 1.72 | 1.52 |
| 1014.5 | 188.8 | — | 183.9 | 1.55 | — |
| 1132.5 | 237.6 | 223.6 | 190.2 | — | — |
| 1198.7 | 211.0 | — | 204.4 | 1.52 | — |
| 1516.7 | — | 273.6 | 233.2 | — | 1.60 |
| 1790.9 | 296.6 | 284.3 | 275.6 | 1.65 | 1.46 |
| 1954.1 | 460.9 | 305.3 | 315.8 | — | — |
| 2215.1 | — | 438.3 | 369.1 | — | — |
| 2230.5 | 391.5 | — | 385.5 | 1.66 | — |
| | | | | Avg: 1.65 + 0.10 | Avg: 1.57 + 0.12 |

What is claimed is:

1. A method for determining the rate of degradation of a nucleic acid biopolymer, comprising;
    a) enriching a first sample nucleic acid biopolymer pool with stable isotope-labeled monomer;
    b) collecting an aliquot of the first sample of nucleic acid biopolymer;
    c) measuring the relative abundance of monoisotopic and isotopomeric peaks in the first sample;
    d) collecting a second aliquot of the first sample of nucleic acid biopolymer;
    e) measuring the relative abundance of monoisotopic and isotopomeric peaks in the second aliquot;
    f) calculating the difference between the relative abundance of monoisotopic and isotopomeric peaks measured for the second sample and the first sample;
    g) dividing the calculated difference between the relative abundance of monoisotopic and isotopomeric peaks by the time duration between the first and second aliquot and therefrom determining the rate of nucleic acid biopolymer degradation.

2. The method of claim 1, wherein the nucleic acid is a DNA, a complementary DNA, a ribosomal DNA, a RNA, a transfer RNA, a messenger RNA, or a nuclear RNA.

3. The method of claim 1, wherein the stable isotope-labeled monomer is a deoxynucleic acid or a ribonucleic acid.

4. The method of claim 1, wherein the nucleic acid biopolymer degradation is measured in an organism, an isolated cell, or a cell free system.

5. The method of claim 1, wherein the nucleic acid biopolymer is separated to form a group of parent nucleic acid biopolymers.

6. The method of claim 5, wherein the parent nucleic acid biopolymer is fragmented.

7. The method of claim 6, wherein the nucleic acid biopolymer is fragmented by means of an enzyme.

8. The method of claim 7, wherein the enzyme is a nuclease.

9. The method of claim 1, wherein the relative abundance of monoisotopic and isotopomeric peaks are corrected for the synthesis of new nucleic acid biopolymer.

10. The method of claim 9, wherein the relative abundance of newly synthesized nucleic acid biopolymer is determined in a second control sample which has been depleted of unlabeled monomer and incubated with stable isotope-labeled monomer for a time period sufficient for new nucleic acid biopolymer synthesis, the relative abundance of monoisotopic and isotopomeric peaks are determined at the time points used for the first sample; and the difference between the relative abundance of monoisotopic and isotopomeric peaks from the first and second sample is determined.

* * * * *

UNITED STATES PATENT AND TRADEMARK OFFICE
CERTIFICATE OF CORRECTION

PATENT NO. : 7,588,887 B2  Page 1 of 1
APPLICATION NO. : 10/722161
DATED : September 15, 2009
INVENTOR(S) : B. Robert Franza, Jr. et al.

It is certified that error appears in the above-identified patent and that said Letters Patent is hereby corrected as shown below:

Column 1, line 18, please delete, "The U.S. government may have certain rights in the invention pursuant to a grant received from the U.S. National Institutes of Health."

and insert

-- This invention was made with government support under grant number P41RR11823 awarded by the National Institutes of Health. The government has certain rights in the invention. --

Signed and Sealed this

Twenty-fourth Day of November, 2009

David J. Kappos
*Director of the United States Patent and Trademark Office*